United States Patent
Tsubata et al.

(10) Patent No.: US 6,313,154 B1
(45) Date of Patent: *Nov. 6, 2001

(54) BIS-THIADIAZOLE DERIVATIVES OR SALTS THEREOF AND AGROHORTICULTURAL DISEASE CONTROLLER AND METHOD FOR USING THE SAME

(75) Inventors: Kenji Tsubata, Kawachinagano; Takashi Shimaoka, Sakai; Kazuhiro Takagi, Osaka; Koji Baba, Kawachinagano; Sohkichi Tajima, Osaka, all of (JP)

(73) Assignee: Nihon Nohyaku Co., Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/276,706

(22) Filed: Mar. 26, 1999

Related U.S. Application Data

(63) Continuation of application No. PCT/JP97/03468, filed on Sep. 29, 1997.

(30) Foreign Application Priority Data

Sep. 30, 1996 (JP) .................................... 8-278949

(51) Int. Cl.[7] .......................... C07D 417/14; A01N 43/82
(52) U.S. Cl. .......................................... 514/361; 548/127
(58) Field of Search .......................... 548/127; 504/261; 514/361

(56) References Cited

U.S. PATENT DOCUMENTS

| 3,914,121 | 10/1975 | Doyle . |
| 3,970,652 | 7/1976 | Doyle . |
| 4,177,054 | 12/1979 | Arndt et al. . |
| 4,314,839 | 2/1982 | Kruger et al. . |
| 4,341,551 | 7/1982 | Kruger et al. . |
| 5,073,563 | 12/1991 | Frickel et al. . |
| 5,227,392 | 7/1993 | Frickel et al. . |

FOREIGN PATENT DOCUMENTS

| 947297 | 5/1974 | (CA) . |
| 0707000 | 4/1996 | (EP) . |
| A-54-9272 | 1/1979 | (JP) . |
| A-2149579 | 6/1990 | (JP) . |
| A-3181463 | 8/1991 | (JP) . |
| A-4234881 | 8/1992 | (JP) . |
| A-09249665 | 9/1997 | (JP) . |
| WO95/01340 | 1/1995 | (WO) . |
| WO96/29871 | 10/1996 | (WO) . |
| 96/29871 | * 10/1996 | (WO) ................................... 548/127 |
| WO98/54163 | 3/1998 | (WO) . |

* cited by examiner

*Primary Examiner*—Robert Gerstl
(74) *Attorney, Agent, or Firm*—Manelli Denison & Selter PLLC; Paul E. White, Jr.

(57) ABSTRACT

A bis-thiadiazole derivative represented by general formula (I):

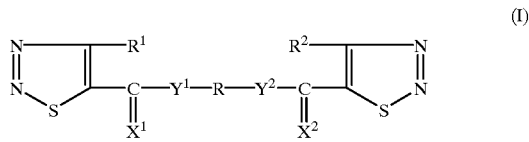

wherein $R^1$ and $R^2$ represent H, $C_1$–$C_8$ alkyl, halo $C_1$–$C_4$ alkyl, unsubstituted or substituted phenyl, 5- or 6-membered heterocycle containing 1 to 3 hetero atoms selected from O, S and N, or the like; $X^1$ and $X^2$ represent O or S; $Y^1$ and $Y^2$ represent O, S or —$N(R^3)$—; R represents $C_0$–$C_{30}$ alkylene. —$(C)_a(R^3)(R^4)$— ($R^3$ and $R^4$ represent H, halogen, OH, $C_1$–$C_4$ alkyl, halo $C_1$–$C_4$ alkyl or the like) or the like; and a is 0 to 30; or a salt thereof, and an agrohorticultural disease controller containing said derivative or salt as an active ingredient.

5 Claims, No Drawings

BIS-THIADIAZOLE DERIVATIVES OR SALTS THEREOF AND AGROHORTICULTURAL DISEASE CONTROLLER AND METHOD FOR USING THE SAME

This is a Continuation International Appln. No. PCT/JP97/03468 filed Sep. 29, 1997 which designated the U.S.

TECHNICAL FIELD

The present invention relates to bis-thiadiazole derivatives or salts thereof and an agrohorticultural disease controller containing said compounds as an active ingredient.

BACKGROUND ART 1,2,3-Thiadiazoles derivatives are disclosed in JP-A-2-149579/1990 as an agent for treating central nervous system diseases, in JP-A-54-9272/1979, JP-A-3-181463/1991, JA-A-4-234881/1992, Canadian Patent 947297, etc. as a herbicide and a plant growth regulator, and in WO 9501340 and JP-A-7-252242/1995 as a fungicide.

DISCLOSURE OF THE INVENTION

With the aim of creating a novel agrohorticultural disease controller, the present inventors have conducted extensive studies to find that the bis-thiadiazole derivatives of the present invention or salts thereof are useful as an agrohorticultural disease controller. Based on this finding, the present invention has been accomplished.

The present invention relates to bis-thiazole derivatives represented by the following general formula (I) or salts thereof, and an agrohorticultural disease controller containing said bis-thiadiazole derivative or a salt thereof as an active ingredient, and a method for using said disease controller:

$$\underset{S}{\overset{N}{\underset{\|}{N}}}\underset{}{\overset{R^1}{\underset{C}{\rule{0pt}{0pt}}}}\underset{X^1}{\overset{\|}{C}}-Y^1-R-Y^2-\underset{X^2}{\overset{\|}{C}}\underset{}{\overset{R^2}{\underset{}{\rule{0pt}{0pt}}}}\underset{S}{\overset{N}{\underset{\|}{N}}} \quad (I)$$

wherein $R^1$ and $R^2$, same or different, represent hydrogen atom, $C_1$–$C_8$ alkyl group, halo $C_1$–$C_4$ alkyl group, phenyl group, substituted phenyl group having 1 to 5 same or different substituents selected from the group consisting of halogen atom, nitro group, cyano group, hydroxyl group, mercapto group, $C_1$–$C_4$ alkyl group, halo $C_1$–$C_4$ alkyl group, $C_1$–$C_4$ alkoxy group, halo $C_1$–$C_4$ alkoxy group, $C_1$–$C_4$ alkylthio group, halo $C_1$–$C_4$ alkylthio group, amino group and substituted amino group having 1 or 2 same or different substituents selected from the group consisting of $C_1$–$C_4$ alkyl and phenyl groups, 5- or 6-membered herocycle containing 1 to 3 same or different hetero atoms selected from the group consisting of oxygen atom, sulfur atom and nitrogen atom, or substituted 5- or 6-membered heterocycle containing 1 to 3 same or different hetero atoms selected from the group consisting of oxygen atom, sulfur atom and nitrogen atom and having 1 to 5 same or different substituents selected from the group consisting of halogen atom, nitro group, cyano group, hydroxyl group, mercapto group, $C_1$–$C_4$ alkyl group, halo $C_1$–$C_4$ alkyl group, $C_1$–$C_4$ alkoxy group, halo $C_1$–$C_4$ alkoxy group, $C_1$–$C_4$ alkylthio group, halo $C_1$–$C_4$ alkylthio group, amino group and substituted amino group having 1 or 2 same or different substituents selected from the group consisting of $C_1$–$C_4$ alkyl and phenyl groups;

$X^1$ and $X^2$, same or different, represent oxygen atom or sulfur atom;

$Y^1$ and $Y^2$, same or different, represent oxygen atom, sulfur atom or

—$N(R^3)$— in which $R^3$ is as defined later; and

R represents $C_0$–$C_{30}$ alkylene group, an alkylene group of the following formula:

$$-\underset{R^4}{\overset{R^3}{\underset{|}{(\overset{|}{C})_a}}}-$$

in which $R^3$ and $R^4$, same or different, represent hydrogen atom, halogen atom, hydroxyl group, nitro group, cyano group, $C_1$–$C_4$ alkyl group, halo $C_1$–$C_4$ alkyl group, $C_1$–$C_4$ alkoxy group, halo $C_1$–$C_4$ alkoxy group, $C_1$–$C_4$ alkylthio group, $C_1$–$C_4$ alkylsulfinyl group, $C_1$–$C_4$ alkylsulfonyl group, hydroxy $C_1$–$C_4$ alkyl group, $C_1$–$C_4$ alkoxy $C_1$–$C_4$ alkyl group, $C_1$–$C_4$ alkoxycarbonyl group, amino group, substituted amino group having 1 or 2 same or different substituents selected from the group consisting of $C_1$–$C_4$ alkyl group, phenyl group and substituted phenyl groups having 1 to 5 same or different substituents selected from the group consisting of halogen atom, nitro group, cyano group, hydroxyl group, mercapto group, $C_1$–$C_4$ alkyl group, halo $C_1$–$C_4$ alkyl group, $C_1$–$C_4$ alkoxy group, halo $C_1$–$C_4$ alkoxy group, $C_1$–$C_4$ alkylthio group, halo $C_1$–$C_4$ alkylthio group, amino group and substituted amino group having 1 or 2 same or different substituents selected from the group consisting of $C_1$–$C_4$ alkyl and phenyl groups, amino $C_1$–$C_4$ alkyl group, substituted amino $C_1$–$C_4$ alkyl group having 1 or 2 same or different substituents selected from $C_1$–$C_4$ alkyl group and substituted phenyl groups having 1 to 5 same or different substituents selected from the group consisting of halogen atom, nitro group, cyano group, hydroxyl group, mercapto group, $C_1$–$C_4$ alkyl group, halo $C_1$–$C_4$ alkyl group, $C_1$–$C_4$ alkoxy group, halo $C_1$–$C_4$ alkoxy group, $C_1$–$C_4$ alkylthio group, halo $C_1$–$C_4$ alkylthio group, amino group and substituted amino group having 1 or 2 same or different substituents selected from the group consisting of $C_1$–$C_4$ alkyl and phenyl groups, phenyl group, substituted phenyl group having 1 to 5 same or different substituents selected from the group consisting of halogen atom, nitro group, cyano group, hydroxyl group, mercapto group, $C_1$–$C_4$ alkyl group, halo $C_1$–$C_4$ alkyl group, $C_1$–$C_4$ alkoxy group, halo $C_1$–$C_4$ alkoxy group, $C_1$–$C_4$ alkylthio group, halo $C_1$–$C_4$ alkylthio group, amino group and substituted amino group having 1 or 2 same or different substituents selected from the group consisting of $C_1$–$C_4$ alkyl and phenyl groups, phenyl $C_1$–$C_4$ alkyl group, substituted phenyl $C_1$–$C_4$ alkyl group having, on the ring thereof, 1 to 5 same or different substituents selected from the group consisting of halogen atom, nitro group, cyano group, hydroxyl group, mercapto group, $C_1$–$C_4$ alkyl group, halo $C_1$–$C_4$ alkyl group, $C_1$–$C_4$ alkoxy group, halo $C_1$–$C_4$ alkoxy group, $C_1$–$C_4$ alkylthio group, halo $C_1$–$C_4$ alkylthio group, amino group and substituted amino group having 1 or 2 same or different substituents selected from the group consisting of $C_1$–$C_4$ alkyl and phenyl groups, phenoxy group, substituted phenoxy group having, on the ring thereof, 1 to 5 same or different substituents selected from the group consisting of halogen atom, nitro group, cyano group, hydroxyl group, mercapto group, $C_1$–$C_4$ alkyl group, halo $C_1$–$C_4$ alkyl group, $C_1$–$C_4$ alkoxy group, halo $C_1$–$C_4$ alkoxy group, $C_1$–$C_4$ alkylthio group, halo $C_1$–$C_4$ alkylthio group, amino group and substituted amino group having 1 or 2 same or different substituents selected from the group consisting of $C_1$–$C_4$ alkyl and phenyl groups, phenoxy $C_1$–$C_4$ alkyl group, substituted phenoxy $C_1$–$C_4$ alkyl group having, on the ring thereof, 1 to 5 same or different substituents selected from the group consisting of halogen atom, nitro group, cyano group, hydroxyl group, mercapto group, $C_1$–$C_4$ alkyl group, halo $C_1$–$C_4$ alkyl group, $C_1$–$C_4$ alkoxy group, halo $C_1$–$C_4$ alkoxy group, $C_1$–$C_4$ alkylthio group, halo $C_1$–$C_4$ alkylthio group, amino group and substituted amino group having 1 or 2 same or different substituents selected from the group consisting of $C_1$–$C_4$ alkyl and phenyl groups, 5- or 6-membered heterocycle containing 1 to 3 same or different hetero atoms selected from the group consisting of oxygen atom, sulfur atom and nitrogen atom, substituted 5- or 6-membered heterocycle containing 1 to 3 same or different hetero atoms selected from the group consisting of oxygen atom, sulfur atom and nitrogen atom and having 1 to 4 same or different substituents selected from the group consisting of halogen atom, nitro group, cyano group, hydroxyl group, mercapto group, $C_1$–$C_4$ alkyl group, halo $C_1$–$C_4$ alkyl group, $C_1$–$C_4$ alkoxy group, halo $C_1$–$C_4$ alkoxy group, $C_1$–$C_4$ alkylthio group, halo $C_1$–$C_4$ alkylthio group, amino group and substituted amino group having 1 or 2 same or different substituents selected from the group consisting of $C_1$–$C_4$ alkyl and phenyl groups, 5- or 6-membered heterocycle $C_1$–$C_4$ alkyl group containing 1 to 3 same or different hetero atoms selected from the group consisting of oxygen atom, sulfur atom and nitrogen atom, substituted 5- or 6-membered hetero cycle $C_1$–$C_4$ alkyl group containing 1 to 3 same or different hetero atoms selected from the group consisting of oxygen atom, sulfur atom and nitrogen atom and having 1 to 4 same or different substituents selected from the group consisting of halogen atom, nitro group, cyano group, hydroxyl group, mercapto group, $C_1$–$C_4$ alkyl group, halo $C_1$–$C_4$ alkyl group, $C_1$–$C_4$ alkoxy group, halo $C_1$–$C_4$ alkoxy group, $C_1$–$C_4$ alkylthio group, halo $C_1$–$C_4$ alkylthio group, amino group and substituted amino group having 1 or 2 same or different substituents selected from the group consisting of $C_1$–$C_4$ alkyl and phenyl groups, or a group

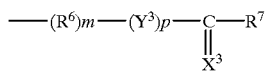

(wherein $R^6$ represents $C_1$–$C_6$ alkylene group, substituted $C_1$–$C_6$ alkylene group substituted by one or more same or different halogen atoms or $C_1$–$C_4$ alkyl groups, or $C_1$–$C_6$ alkylene group which may be intercepted by
—O—,
—S(O)$_n$—
in which n is an integer of 0–2, or
—N(R$^8$)—

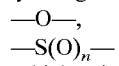

in which $R^8$ represents hydrogen atom, halogen atom, $C_1$–$C_4$ alkyl group, halo $C_1$–$C_4$ alkyl group, $C_1$–$C_4$ alkoxycarbonyl group, phenyl group, substituted phenyl group having 1 to 5 same or different substituents selected from the group consisting of halogen atom, nitro group, cyano group, hydroxyl group, mercapto group, $C_1$–$C_4$ alkyl group, halo $C_1$–$C_4$ alkyl group, $C_1$–$C_4$ alkoxy group, halo $C_1$–$C_4$ alkoxy group, $C_1$–$C_4$ alkylthio group, halo $C_1$–$C_4$ alkylthio group, amino group and substituted amino group having 1 or 2 same or different substituents selected from the group consisting of $C_1$–$C_4$ alkyl and phenyl groups, phenyl $C_1$–$C_4$ alkyl group, substituted phenyl $C_1$–$C_4$ alkyl group having 1 to 5 same or different substituents selected from the group consisting of halogen atom, nitro group, cyano group, hydroxyl group, mercapto group, $C_1$–$C_4$ alkyl group, halo $C_1$–$C_4$ alkyl group, $C_1$–$C_4$ alkoxy group, halo $C_1$–$C_4$ alkoxy group, $C_1$–$C_4$ alkylthio group, halo $C_1$–$C_4$ alkylthio group, amino group and substituted amino group having 1 or 2 same or different substituents selected from the group consisting of $C_1$–$C_4$ alkyl and phenyl groups, or

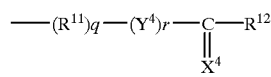

(wherein $R^{11}$ represents $C_1$–$C_6$ alkylene group or substituted $C_1$–$C_6$ alkylene group having one or more substituents selected from the group consisting of halogen atom and $C_1$–$C_4$ alkyl group;

$R^{12}$ represents hydrogen atom, $C_1$–$C_8$ alkyl group, halo $C_1$–$C_4$ alkyl group, phenyl group, substituted phenyl group having 1 to 5 same or different substituents selected from the group consisting of halogen atom, nitro group, cyano group, hydroxyl group, mercapto group, $C_1$–$C_4$ alkyl group, halo $C_1$–$C_4$ alkyl group, $C_1$–$C_4$ alkoxy group, halo $C_1$–$C_4$ alkoxy group, $C_1$–$C_4$ alkylthio group, halo $C_1$–$C_4$ alkylthio group, amino group and substituted amino group having 1 or 2 same or different substituents selected from the group consisting of $C_1$–$C_4$ alkyl and phenyl groups, 5- or 6-membered heterocycle containing 1 to 3 same or different hetero atoms selected from the group consisting of oxygen atom, sulfur atom and nitrogen atom, or substituted 5- or 6-membered heterocycle containing 1 to 3 same or different hetero atoms selected from the group consisting of oxygen atom, sulfur atom and nitrogen atom and having 1 to 4 same or different substituents selected from the group consisting of halogen atom, nitro group, cyano group, hydroxyl group, mercapto group, $C_1$–$C_4$ alkyl group, halo $C_1$–$C_4$ alkyl group, $C_1$–$C_4$ alkoxy group, halo $C_1$–$C_4$ alkoxy group, $C_1$–$C_4$ alkylthio group, halo $C_1$–$C_4$ alkylthio group, amino group and substituted amino group having 1 or 2 same or different substituents selected from the group consisting of $C_1$–$C_4$ alkyl and phenyl groups;

$Y^4$ represents
—O—,
—S— or
—N(R$^{13}$)— in which $R^{13}$ represents hydrogen atom or $C_1$–$C_4$ alkyl group;

$X^4$ represents oxygen atom or sulfur atom;

q represents an integer of 0 to 1; and r represents an integer of 0 to 1);

$R^7$ represents hydrogen atom, $C_1$–$C_8$ alkyl group, halo $C_1$–$C_8$ alkyl group, phenyl group, substituted phenyl group having 1 to 5 same or different substituents selected from the group consisting of halogen atom, nitro group, cyano group, hydroxyl group, mercapto group, $C_1$–$C_4$ alkyl group, halo $C_1$–$C_4$ alkyl group, $C_1$–$C_4$ alkoxy group, halo $C_1$–$C_4$ alkoxy group, $C_1$–$C_4$ alkylthio group, halo $C_1$–$C_4$ alkylthio group, amino group and substituted amino group having 1 or 2 same or different substituents selected from the group consisting of $C_1$–$C_4$ alkyl and phenyl groups, phenyl $C_1$–$C_4$ alkyl group, substituted phenyl $C_1$–$C_4$ alkyl group having, on the ring thereof, 1 to 5 same or different substituents selected from the group consisting of halogen atom, nitro group, cyano group, hydroxyl group, mercapto group, $C_1$–$C_4$ alkyl group, halo $C_1$–$C_4$ alkyl group, $C_1$–$C_4$ alkoxy group, halo $C_1$–$C_4$ alkoxy group, $C_1$–$C_4$ alkylthio group, halo $C_1$–$C_4$ alkylthio group, amino group and substituted amino group having 1 or 2 same or different substituents selected from the group consisting of $C_1$–$C_4$ alkyl and phenyl groups, 5- or 6-membered heterocycle containing 1 to 3 same or different hetero atoms selected from the group consisting of oxygen atom, sulfur atom and nitrogen atom, or substituted 5- or 6-membered heterocycle containing 1 to 3 same or different hetero atoms selected from the group consisting of oxygen atom, sulfur atom and nitrogen atom and having, on the ring thereof, 1 to 5 same or different substituents selected from the group consisting of halogen atom, nitro group, cyano group, hydroxyl group, mercapto group, $C_1$–$C_4$ alkyl group, halo $C_1$–$C_4$ alkyl group, $C_1$–$C_4$ alkoxy group, halo $C_1$–$C_4$ alkoxy group, $C_1$–$C_4$ alkylthio group, halo $C_1$–$C_4$ alkylthio group, amino group and substituted amino group having 1 or 2 same or different substituents selected from the group consisting of $C_1$–$C_4$ alkyl and phenyl groups;

$Y^3$ represents

—O—,

—S— or

—N($R^8$)— in which $R^8$ is as defined above;

$X^3$ represents oxygen atom or sulfur atom;

m represents an integer of 0 to 5; and p represents an integer of 0 or 1; and letter a represents an integer of 0 to 30;

further, $R^3$ and $R^4$ may be taken conjointly to form a 3- to 8-membered ring including a $C_0$–$C_7$ alkylene group, and said 3- to 8-membered ring may be intercepted by

—O—,

—S(O)$_n$— in which n represents an integer of 0–2,

—N($R^8$)— in which $R^8$ is as defined above, or

—C($R^9$)($R^{10}$)— in which $R^9$ and $R^{10}$, same or different, represent halogen atom, $C_1$–$C_4$ alkyl group or a group of the following formula:

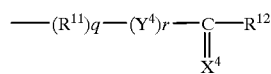

in which $R^{11}$, $R^{12}$, $X^4$, $Y^4$, q and r are as defined above; and $R^9$ and $R^{10}$ may be taken conjointly to form a 3- to 7-membered ring including a $C_2$–$C_6$ alkylene group; and R alternatively represents $C_0$–$C_{30}$ alkylene group which may be intercepted by one or more same or different group selected from the group consisting of

—O—,

—S(O)$_n$— in which n is as defined above,

—N($R^3$)— in which $R^3$ is as defined above,

—C($R^3$)=C($R^4$)— in which $R^3$ and $R^4$ are as defined above,

—C≡C—,

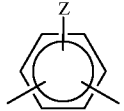

(Z represents halogen atom, nitro group, cyano group, hydroxyl group, mercapto group, $C_1$–$C_4$ alkyl group, halo $C_1$–$C_4$ alkyl group, $C_1$–$C_4$ alkoxy group, halo $C_1$–$C_4$ alkoxy group, $C_1$–$C_4$ alkylthio group, halo $C_1$–$C_4$ alkylthio group, amino group, substituted amino group having 1 or 2 same or different substituents selected from the group consisting of $C_1$–$C_4$ alkyl and phenyl groups, or a group of the following formula:

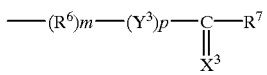

in which $R^6$, $R^7$, $Y^3$, $X^3$, m and p are as defined above) and

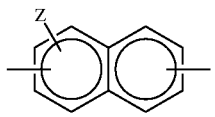

(Z is as defined above).

BEST MODE FOR CARRYING OUT THE INVENTION

In the definitions of the substituents in the bis-thiadiazole derivatives of the present invention represented by general formula (I), the term "halogen atom" means chlorine atom, bromine atom, iodine atom or fluorine atom; the term "$C_1$–$C_8$ alkyl group" means a straight or branched chain alkyl group having 1 to 8 carbon atoms such as methyl, ethyl, n-propyl, i-propyl, n-butyl, i-butyl, s-butyl, t-butyl, n-pentyl, n-hexyl, n-heptyl, n-octyl and the like; the term "halo $C_1$–$C_4$ alkyl group" means an same or different straight or branched chain alkyl group substituted by at least one halogen atom; and the term "5- or 6-membered heterocycle containing 1 to 3 same or different hetero atoms selected from the group consisting of oxygen atom, nitrogen atom and sulfur atom" means a 5- or 6-membered heterocycle such as furan, thiophene, pyrrole, oxazole, thiazole, isothiazole, pyrazole, imidazole, 1,2,3-thiadiazole, 1,2,4-thiadiazole, 1,2,5-thiadiazole, 1,3,4-thiadiazole, 1,2,4-triazole, pyridine, pyridazine, pyrimidine, pyrazine, pyrrolidine, piperidine, morpholine, thiomorpholine, dithiolane, dithiane, piperazine, dioxalane, imidazolidine and the like.

As examples of the salt of the bis-thiadiazole derivative represented by general formula (I), there can be referred to salts of alkali metals such as sodium, potassium and the like, salts of alkaline earth metals such as calcium, magnesium and the like, ammonium salts, substituted ammonium salts substituted by one or more same or different substituents selected from the group consisting of $C_1$–$C_{12}$ alkyl group, phenyl group, substituted phenyl group, benzyl group and substituted benzyl group, guanidium salt and the like.

As preferred substituents in the general formula (I) of the present invention, the following can be referred to. Thus, as $R^1$ and $R^2$ which may be same or different, methyl group, ethyl group, i-propyl group, cyclopropyl group and the like are preferred. As $X^1$ and $X^2$, oxygen atom is preferred. As $Y^1$ and $Y^2$, oxygen atom and —NH— are preferred. As R, preferred are phenylene group, alkylene group having 2–6 carbon atoms, —$(CH_2CH_2O)_{1-3}$— and a group of the following formula:

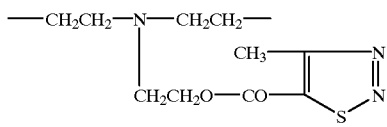

The bis-thiadiazole derivatives of the present invention represented by formula (I) or salts thereof can be produced, for example, by the following production processes.

PRODUCTION PROCESS 1

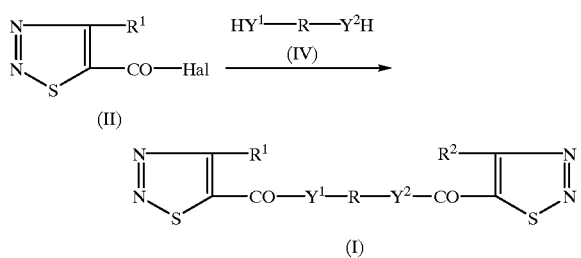

wherein R, $R^1$, $R^2$, $Y^1$ and $Y^2$ are as defined above and Hal represents halogen atom.

A bis-thiadiazole derivative represented by general formula (I) can be produced by reacting a compound represented by general formula (II) with a compound represented by general formula (IV) in the absence or presence of a base, in the absence or presence of an inert solvent.

This reaction can be performed according to the method described in "Shin Jikken Kagaku Koza", Vol. 15 (II), p.1012 (Maruzen K. K.) and ibid. p.1142.

PRODUCTION PROCESS 2

(a case where $Y^1$ and $Y^2$ are oxygen atoms)

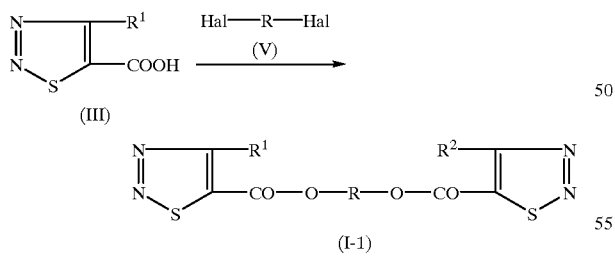

wherein R, $R^1$, $R^2$ and Hal are as defined above.

A bis-thiadiazole derivative represented by general formula (I—I) can be produced by reacting a compound represented by general formula (III) with a compound represented by general formula (V) in the presence or absence of a base, in the presence or absence of an inert solvent.

This reaction can be performed according to the description of "Shin Jikken Kagaku Koza", Vol. 15 (II), p. 1008.

PRODUCTION PROCESS 3

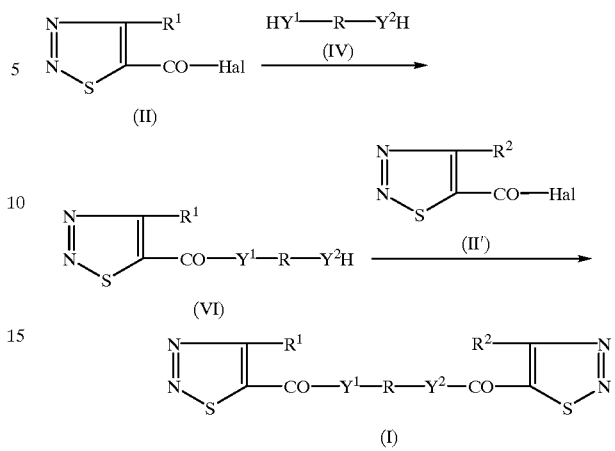

wherein R, $R^1$, $R^2$, $Y^1$, $Y^2$ and Hal are as defined above.

A bis-thiadiazole derivative represented by general formula (I) can be produced by reacting a compound represented by general formula (II) with a compound represented by general formula (IV) in the presence or absence of a base, in the presence or absence of an inert solvent to form a thiadiazole derivative represented by general formula (VI), and after isolating the compound (VI) or without isolating (VI), reacting the compound (VI) with a compound represented by general formula (II').

This reaction can be performed according to the known method described in the paragraph of Method 1.

The compounds represented by general formulas (II) and (III) which are starting compounds in the Production process 1 and 2 can be produced, for example, by the known method described below.

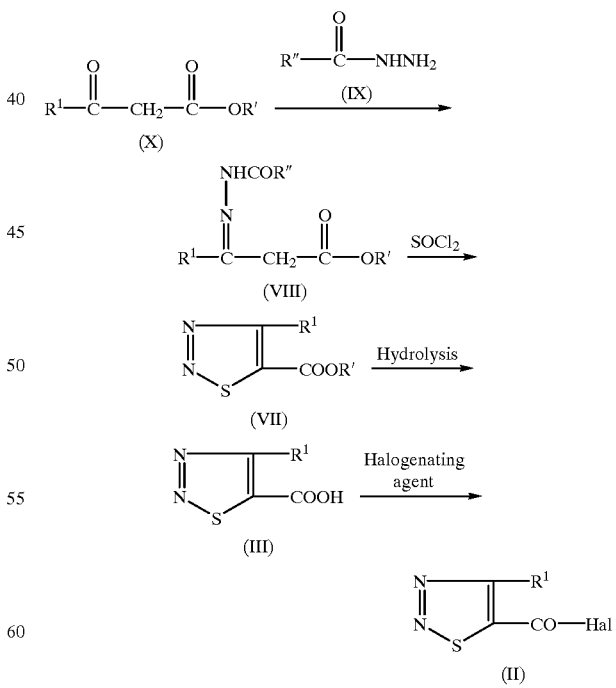

wherein $R^1$ and Hal are as defined above, R' represents $C_1$–$C_8$ alkyl group, and R" represents $C_1$–$C_4$ alkyl group, $C_1$–$C_4$ alkoxy group or an amino group which may have a substituent.

A compound represented by general formula (II) can be produced by reacting a compound represented by general formula (X) with a compound represented by general formula (IX) to form a compound represented by general formula (VIII) and, after isolating the compound (VIII) or without isolating (VIII), subjecting the compound (VIII) to a ring closure reaction using thionyl chloride to form a compound represented by general formula (VII), and after isolating the compound (VII) or without isolating (VII), hydrolyzing the compound (VII) to form a compound represented by general formula (III), and after isolating the compound (III) or without isolating (III), halogenating the compound (III) with a halogenating agent.

This reaction can be performed according to a known method described in J. Am. Chem. Soc., 77, 5359 (1955), etc.

The compound represented by general formula (II') can also be produced by the same method as above.

Next, typical examples of the bis-thiadiazole derivative of the present invention represented by general formula (I) will be mentioned below. The present invention is by no means limited by these examples.

In Table 1, meanings of the abbreviations are as follows:

Me: methyl group, Et: ethyl group, Pr: propyl group,
Bu: butyl group, Ph: phenyl or phenylene group,

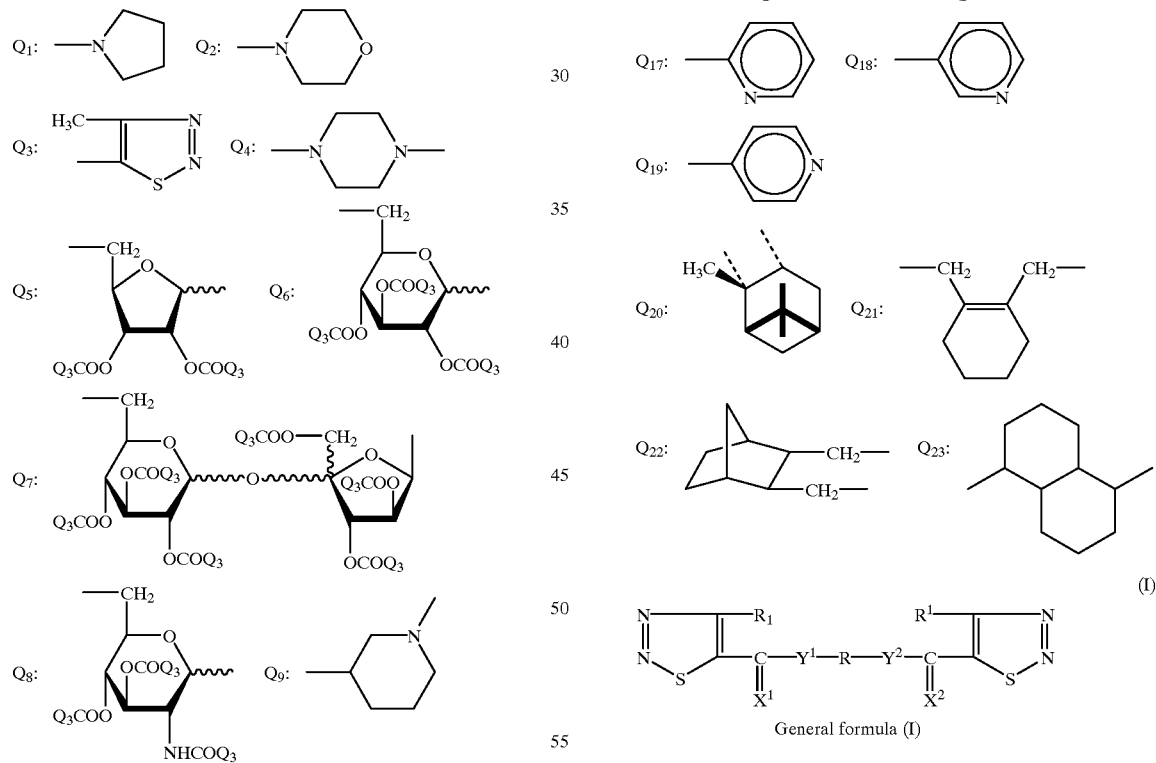

General formula (I)

TABLE 1

| No | $R^1$ | $X^1$ | $Y^1$ | R | $R^2$ | $X^2$ | $Y^2$ |
|---|---|---|---|---|---|---|---|
| 1 | Me | O | O | $CH_2$ | Me | O | O |
| 2 | Me | O | O | $(CH_2)_2$ | Me | O | O |
| 3 | Me | O | O | $(CH_2)_3$ | Me | O | O |
| 4 | Me | O | O | $(CH_2)_4$ | Me | O | O |
| 5 | Me | O | O | $(CH_2)_5$ | Me | O | O |

TABLE 1-continued

| No | $R^1$ | $X^1$ | $Y^1$ | R | $R^2$ | $X^2$ | $Y^2$ |
|---|---|---|---|---|---|---|---|
| 6 | Me | O | O | $(CH_2)_6$ | Me | O | O |
| 7 | Me | O | O | $(CH_2)_7$ | Me | O | O |
| 8 | Me | O | O | $(CH_2)_8$ | Me | O | O |
| 9 | Me | O | O | $(CH_2)_9$ | Me | O | O |
| 10 | Me | O | O | $(CH_2)_{10}$ | Me | O | O |
| 11 | Me | O | O | $(CH_2)_{11}$ | Me | O | O |
| 12 | Me | O | O | $(CH_2)_{12}$ | Me | O | O |
| 13 | Me | O | O | $(CH_2)_{13}$ | Me | O | O |
| 14 | Me | O | O | $(CH_2)_{14}$ | Me | O | O |
| 15 | Me | O | O | $(CH_2)_{15}$ | Me | O | O |
| 16 | Me | O | O | $(CH_2)_{16}$ | Me | O | O |
| 17 | Me | O | O | $(CH_2)_{17}$ | Me | O | O |
| 18 | Me | O | O | $(CH_2)_{18}$ | Me | O | O |
| 19 | Me | O | O | $(CH_2)_{19}$ | Me | O | O |
| 20 | Me | O | O | $(CH_2)_{20}$ | Me | O | O |
| 21 | Me | O | O | $CH_2CH(Me)$ | Me | O | O |
| 22 | Me | O | O | $CH_2CH(CH_2F)$ | Me | O | O |
| 23 | Me | O | O | $CH_2CH(CH_2Cl)$ | Me | O | O |
| 24 | Me | O | O | $CH_2CH(CH_2Br)$ | Me | O | O |
| 25 | Me | O | O | $CH_2CH(Et)$ | Me | O | O |
| 26 | Me | O | O | $CH_2CH(n\text{-}Pr)$ | Me | O | O |
| 27 | Me | O | O | $CH_2CH(i\text{-}Pr)$ | Me | O | O |
| 28 | Me | O | O | $CH_2CH(n\text{-}Bu)$ | Me | O | O |
| 29 | Me | O | O | $CH_2CH(i\text{-}Bu)$ | Me | O | O |
| 30 | Me | O | O | $CH_2CH(t\text{-}Bu)$ | Me | O | O |
| 31 | Me | O | O | $CH_2CH(n\text{-}C_6H_{13})$ | Me | O | O |
| 32 | Me | O | O | $CH_2CH(n\text{-}C_8H_{17})$ | Me | O | O |
| 33 | Me | O | O | $CH_2CH(n\text{-}C_{10}H_{21})$ | Me | O | O |
| 34 | Me | O | O | $CH_2CH(n\text{-}C_{12}H_{25})$ | Me | O | O |
| 35 | Me | O | O | $CH_2CH(Ph)$ | Me | O | O |
| 36 | Me | O | O | $CH_2CH(2\text{-}Cl\text{—}Ph)$ | Me | O | O |
| 37 | Me | O | O | $CH_2CH(3\text{-}Cl\text{—}Ph)$ | Me | O | O |
| 38 | Me | O | O | $CH_2CH(4\text{-}Cl\text{—}Ph)$ | Me | O | O |
| 39 | Me | O | O | $CH_2CH(2\text{-}Me\text{—}Ph)$ | Me | O | O |
| 40 | Me | O | O | $CH_2CH(3\text{-}Me\text{—}Ph)$ | Me | O | O |
| 41 | Me | O | O | $CH_2CH(4\text{-}Me\text{—}Ph)$ | Me | O | O |
| 42 | Me | O | O | $CH_2CH(4\text{-}i\text{-}Pr\text{—}Ph)$ | Me | O | O |
| 43 | Me | O | O | $CH_2CH(3\text{-}i\text{-}PrO\text{—}Ph)$ | Me | O | O |
| 44 | Me | O | O | $CH_2CH(4\text{-}Br\text{—}Ph)$ | Me | O | O |
| 45 | Me | O | O | $CH_2CH(4\text{-}CF_3\text{—}Ph)$ | Me | O | O |
| 46 | Me | O | O | $CH(Me)CH(Me)$ | Me | O | O |
| 47 | Me | O | O | $CH_2C(Me)_2$ | Me | O | O |
| 48 | Me | O | O | $CH(Me)C(Me)_2$ | Me | O | O |
| 49 | Me | O | O | $C(Me)_2C(Me)_2$ | Me | O | O |
| 50 | Me | O | O | $CH_2CH(CH_2OMe)$ | Me | O | O |
| 51 | Me | O | O | $CH_2CH(CH_2OPh)$ | Me | O | O |
| 52 | Me | O | O | $CH_2CH(CH_2O(3\text{-}Cl\text{—}Ph))$ | Me | O | O |
| 53 | Me | O | O | $CH_2CH(CH_2O(4\text{-}MeO\text{—}Ph))$ | Me | O | O |
| 54 | Me | O | O | $CH_2CH(CH_2O\text{—}CH_2Ph)$ | Me | O | O |
| 55 | Me | O | O | $CH_2CH(CH_2O\text{—}COMe)$ | Me | O | O |
| 56 | Me | O | O | $CH_2CH(CH_2O\text{—}COBu\text{-}t)$ | Me | O | O |
| 57 | Me | O | O | $CH_2CH(CH_2O\text{—}COPh)$ | Me | O | O |
| 58 | Me | O | O | $CH_2CH(CH_2O\text{—}CO(2\text{-}Cl\text{—}Ph))$ | Me | O | O |
| 59 | Me | O | O | $CH_2CH(CH_2O\text{—}CO(3\text{-}Cl\text{—}Ph))$ | Me | O | O |
| 60 | Me | O | O | $CH_2CH(CH_2O\text{—}CO(4\text{-}Cl\text{—}Ph))$ | Me | O | O |
| 61 | Me | O | O | $CH_2CH(CH_2O\text{—}CO(4\text{-}CF_3\text{—}Ph))$ | Me | O | O |
| 62 | Me | O | O | $CH_2CH(CH_2SMe)$ | Me | O | O |
| 63 | Me | O | O | $CH_2CH(CH_2SOMe)$ | Me | O | O |
| 64 | Me | O | O | $CH_2CH(CH_2SO_2Me)$ | Me | O | O |
| 65 | Me | O | O | $CH_2CH(CH_2N(Me)_2)$ | Me | O | O |
| 66 | Me | O | O | $CH_2CH(CH_2N(Et)_2)$ | Me | O | O |
| 67 | Me | O | O | $CH_2CH(CH_2\text{—}Q_1)$ | Me | O | O |
| 68 | Me | O | O | $CH_2CH(CH_2\text{—}Q_2)$ | Me | O | O |
| 69 | Me | O | O | $CH_2CH(CH_2NHCOMe)$ | Me | O | O |
| 70 | Me | O | O | $CH_2CH(CH_2NHCOEt)$ | Me | O | O |
| 71 | Me | O | O | $CH_2CH(CH_2NHCOPr\text{-}i)$ | Me | O | O |
| 72 | Me | O | O | $CH_2CH(CH_2NHCOBu\text{-}n)$ | Me | O | O |
| 73 | Me | O | O | $CH_2CH(CH_2NHCOPh)$ | Me | O | O |
| 74 | Me | O | O | $CH_2CH(CH_2NHCO(2\text{-}Cl\text{—}Ph))$ | Me | O | O |
| 75 | Me | O | O | $CH_2CH(CH_2NHCO(3\text{-}Cl\text{—}Ph))$ | Me | O | O |
| 76 | Me | O | O | $CH_2CH(CH_2NHCO(4\text{-}Cl\text{—}Ph))$ | Me | O | O |
| 77 | Me | O | O | $CH_2CH(CN)$ | Me | O | O |
| 78 | Me | O | O | $CH(Ph)CH(Ph)$ (meso) | Me | O | O |
| 79 | Me | O | O | $CH(Ph)CH(Ph)$ (+/−) | Me | O | O |
| 80 | Me | O | O | $CH_2CH_2CH(Me)$ | Me | O | O |
| 81 | Me | O | O | $CH_2CH(Me)CH_2$ | Me | O | O |
| 82 | Me | O | O | $CH_2C(Me)_2CH_2$ | Me | O | O |

TABLE 1-continued

| No | R¹ | X¹ | Y¹ | R | R² | X² | Y² |
|---|---|---|---|---|---|---|---|
| 83 | Me | O | O | CH$_2$C(CH$_2$Br)$_2$CH$_2$ | Me | O | O |
| 84 | Me | O | O | CH(Me)CH$_2$CH(Me) | Me | O | O |
| 85 | Me | O | O | CH(Me)CH$_2$C(Me)$_2$ | Me | O | O |
| 86 | Me | O | O | C(Me)$_2$CH$_2$C(Me)$_2$ | Me | O | O |
| 87 | Me | O | O | CH$_2$C(Me)(Et)CH$_2$ | Me | O | O |
| 88 | Me | O | O | CH$_2$C(Et)$_2$CH$_2$ | Me | O | O |
| 89 | Me | O | O | CH$_2$C(Me)(n-Pr)CH$_2$ | Me | O | O |
| 90 | Me | O | O | CH(i-Pr)C(Me)$_2$CH$_2$ | Me | O | O |
| 91 | Me | O | O | CH(n-Pr)C(Et)$_2$CH$_2$ | Me | O | O |
| 92 | Me | O | O | CH$_2$C(Et)(n-Bu)CH$_2$ | Me | O | O |
| 93 | Me | O | O | CH$_2$C(Me)(CH$_2$O—COQ$_3$)CH$_2$ | Me | O | O |
| 94 | Me | O | O | CH$_2$C(NO$_2$)(CH$_2$O—COQ$_3$)CH$_2$ | Me | O | O |
| 95 | Me | O | O | CH$_2$C(Et)(CH$_2$O—COQ$_3$)CH$_2$ | Me | O | O |
| 96 | Me | O | O | CH$_2$C(Et)(CH$_2$O—COQ$_3$)CH$_2$ | Me | O | O |
| 97 | Me | O | O | CH$_2$CH(Cl)CH$_2$ | Me | O | O |
| 98 | Me | O | O | CH$_2$CH(Br)CH$_2$ | Me | O | O |
| 99 | Me | O | O | CH$_2$C(Br)(NO$_2$)CH$_2$ | Me | O | O |
| 100 | Me | O | O | CH$_2$CH(OH)CH$_2$ | Me | O | O |
| 101 | Me | O | O | CH$_2$CH(OMe)CH$_2$ | Me | O | O |
| 102 | Me | O | O | CH$_2$CH(OCH$_2$Ph)CH$_2$ | Me | O | O |
| 103 | Me | O | O | CH$_2$CH(O—COMe)CH$_2$ | Me | O | O |
| 104 | Me | O | O | CH$_2$CH(O—COPh)CH$_2$ | Me | O | O |
| 105 | Me | O | O | CH$_2$CH(O—CO(4-Cl—Ph))CH$_2$ | Me | O | O |
| 106 | Me | O | O | CH$_2$CH(O—COQ$_3$)CH$_2$ | Me | O | O |
| 107 | Me | O | O | CH$_2$CH(O—COOMe)CH$_2$ | Me | O | O |
| 108 | Me | O | O | CH$_2$CH(NH$_2$)CH$_2$ | Me | O | O |
| 109 | Me | O | O | CH$_2$C(Me)(NHCOQ$_3$)CH$_2$ | Me | O | O |
| 110 | Me | O | O | CH$_2$C(Et)(NHCOQ$_3$)CH$_2$ | Me | O | O |
| 111 | Me | O | O | CH$_2$C(CH$_2$COQ$_3$)(NHCOQ$_3$)CH$_2$ | Me | O | O |
| 112 | Me | O | O | CH$_2$CH(NHCOMe)CH$_2$ | Me | O | O |
| 113 | Me | O | O | CH$_2$CH(NHCOPh)CH$_2$ | Me | O | O |
| 114 | Me | O | O | CH$_2$CH(NHCOQ$_3$)CH$_2$ | Me | O | O |
| 115 | Me | O | O | CH$_2$CH(SMe)CH$_2$ | Me | O | O |
| 116 | Me | O | O | CH$_2$C(COOMe)$_2$CH$_2$ | Me | O | O |
| 117 | Me | O | O | CH$_2$C(COOEt)$_2$CH$_2$ | Me | O | O |
| 118 | Me | O | O | CH$_2$C(COOPr-i)$_2$CH$_2$ | Me | O | O |
| 119 | Me | O | O | CH$_2$C(CN)$_2$CH$_2$ | Me | O | O |
| 120 | Me | O | O | CH$_2$CH$_2$C(Me)$_2$ | Me | O | O |
| 121 | Me | O | O | CH(Me)CH$_2$C(Me)$_2$ | Me | O | O |
| 122 | Me | O | O | CH(Me)CH$_2$CH$_2$C(Me)$_2$ | Me | O | O |
| 123 | Me | O | O | CH$_2$CH(Cl)CH(Cl)CH$_2$ | Me | O | O |
| 124 | Me | O | O | CH$_2$CH(Br)CH(Br)CH$_2$ | Me | O | O |
| 125 | Me | O | O | CH$_2$CH$_2$CH(OH)CH$_2$ | Me | O | O |
| 126 | Me | O | O | CH$_2$CH$_2$CH(O—COQ$_3$)CH$_2$ | Me | O | O |
| 127 | Me | O | O | CH$_2$CH(O—COQ$_3$)CH(O—COQ$_3$)CH$_2$ | Me | O | O |
| 128 | Me | O | O | CH$_2$CH(COOMe)CH(COOMe)CH$_2$ | Me | O | O |
| 129 | Me | O | O | CH$_2$CH(COOEt)CH(COOEt)CH$_2$ | Me | O | O |
| 130 | Me | O | O | CH$_2$CH$_2$CH$_2$CH(Me) | Me | O | O |
| 131 | Me | O | O | CH$_2$CH$_2$CH$_2$CH$_2$CH(Me) | Me | O | O |
| 132 | Me | O | O | (CH$_2$)$_3$C(NO$_2$)((CH$_2$)$_3$O—COQ$_3$)(CH$_2$)$_3$ | Me | O | O |
| 133 | Me | O | O | CH$_2$CH=CHCH$_2$ (E) | Me | O | O |
| 134 | Me | O | O | CH$_2$CH=CHCH$_2$ (Z) | Me | O | O |
| 135 | Me | O | O | CH$_2$C(Me)=C(Me)CH$_2$ (E) | Me | O | O |
| 136 | Me | O | O | CH$_2$CH=C(Me)CH$_2$ (E) | Me | O | O |
| 137 | Me | O | O | CH$_2$CH=C(Me)CH$_2$ (Z) | Me | O | O |
| 138 | Me | O | O | CH$_2$CH=C(Cl)CH$_2$ (E) | Me | O | O |
| 139 | Me | O | O | CH$_2$CH=C(Cl)CH$_2$ (Z) | Me | O | O |
| 140 | Me | O | O | CH$_2$C≡CCH$_2$ | Me | O | O |
| 141 | Me | O | O | 1-cyclo-C$_5$H$_8$-2 | Me | O | O |
| 142 | Me | O | O | 1-cyclo-C$_5$H$_8$-3 | Me | O | O |
| 143 | Me | O | O | 1-cyclo-C$_6$H$_{10}$-2 | Me | O | O |
| 144 | Me | O | O | 1-cyclo-C$_6$H$_{10}$-3 | Me | O | O |
| 145 | Me | O | O | 1-cyclo-C$_6$H$_{10}$-4 | Me | O | O |
| 146 | Me | O | O | Q$_{20}$ | Me | O | O |
| 147 | Me | O | O | 1-(5-O-COQ$_3$-cyclo-C$_5$H$_{10}$)-3 | Me | O | O |
| 148 | Me | O | O | CH$_2$-1-cyclo-C$_6$H$_{10}$-1 | Me | O | O |
| 149 | Me | O | O | CH$_2$-1-cyclo-C$_6$H$_{10}$-2-CH$_2$ | Me | O | O |
| 150 | Me | O | O | Q$_{21}$ | Me | O | O |
| 151 | Me | O | O | Q$_{22}$ | Me | O | O |
| 152 | Me | O | O | 1-cyclo-C$_8$H$_{14}$-2 | Me | O | O |
| 153 | Me | O | O | Q$_{23}$ | Me | O | O |
| 154 | Me | O | O | 1-Ph-2 | Me | O | O |
| 155 | Me | O | O | 1-Ph-3 | Me | O | O |
| 156 | Me | O | O | 1-Ph-4 | Me | O | O |
| 157 | Me | O | O | 1-(3-F—Ph)-2 | Me | O | O |
| 158 | Me | O | O | 1-(3-Me—Ph)-2 | Me | O | O |
| 159 | Me | O | O | 1-(3-MeO—Ph)-2 | Me | O | O |

TABLE 1-continued

| No | R¹ | X¹ | Y¹ | R | R² | X² | Y² |
|---|---|---|---|---|---|---|---|
| 160 | Me | O | O | 1-(4-Cl—Ph)-3 | Me | O | O |
| 161 | Me | O | O | 1-(4,6-Cl₂—Ph)-3 | Me | O | O |
| 162 | Me | O | O | 1-(5-Me—Ph)-3 | Me | O | O |
| 163 | Me | O | O | 1-(4-Et—Ph)-3 | Me | O | O |
| 164 | Me | O | O | 1-(5-C₅H₁₁—Ph)-3 | Me | O | O |
| 165 | Me | O | O | 1-(5-OMe—Ph)-3 | Me | O | O |
| 166 | Me | O | O | 1-(5-O—COQ₃—Ph)-3 | Me | O | O |
| 167 | Me | O | O | 1-(2-Cl—Ph)-4 | Me | O | O |
| 168 | Me | O | O | 1-(2-Me—Ph)-4 | Me | O | O |
| 169 | Me | O | O | 1-(2,3,5-Me₃—Ph)-4 | Me | O | O |
| 170 | Me | O | O | (dimethylnaphthalene structure) | Me | O | O |
| 171 | Me | O | O | (dimethylnaphthalene structure) | Me | O | O |
| 172 | Me | O | O | (dimethylnaphthalene structure) | Me | O | O |
| 173 | Me | O | O | (dimethylnaphthalene structure) | Me | O | O |
| 174 | Me | O | O | (biphenyl structure) | Me | O | O |
| 175 | Me | O | O | —Ph—CH₂—Ph— | Me | O | O |
| 176 | Me | O | O | —Ph—C(Me)₂—Ph— | Me | O | O |
| 177 | Me | O | O | —Ph—C(CF₃)₂—Ph— | Me | O | O |
| 178 | Me | O | O | CH(Et)CH(Et) | Me | O | O |
| 179 | Me | O | O | —Ph—C(Et)=C(Et)—Ph— | Me | O | O |
| 180 | Me | O | O | —CH₂—Ph—OMe | Me | O | O |

TABLE 1-continued

| No | $R^1$ | $X^1$ | $Y^1$ | R | $R^2$ | $X^2$ | $Y^2$ |
|---|---|---|---|---|---|---|---|
| 181 | Me | O | O | -CH₂-(2-Me,5-OMe-phenyl) | Me | O | O |
| 182 | Me | O | O | -(4-Me-phenyl)-CH₂- | Me | O | O |
| 183 | Me | O | O | -CH₂-(1,3-phenylene)-CH₂- | Me | O | O |
| 184 | Me | O | O | -CH₂-(1,4-phenylene)-CH₂- | Me | O | O |
| 185 | Me | O | O | -CH₂-(2,3,5,6-tetramethyl-1,4-phenylene)-CH₂- | Me | O | O |
| 186 | Me | O | O | -C(Me)₂-(1,4-phenylene)-C(Me)₂- | Me | O | O |
| 187 | Me | O | O | $CH_2CH_2OCH_2CH_2$ | Me | O | O |
| 188 | Me | O | O | $CH_2CH_2(OCH_2CH_2)_2$ | Me | O | O |
| 189 | Me | O | O | $CH_2CH_2(OCH_2CH_2)_3$ | Me | O | O |
| 190 | Me | O | O | $CH_2CH_2(OCH_2CH_2)_4$ | Me | O | O |
| 191 | Me | O | O | $CH_2CH_2(OCH_2CH_2)_5$ | Me | O | O |
| 192 | Me | O | O | $CH_2CH_2(OCH_2CH_2)_6$ | Me | O | O |
| 193 | Me | O | O | $CH_2CH_2(OCH_2CH_2)_7$ | Me | O | O |
| 194 | Me | O | O | $CH_2CH_2(OCH_2CH_2)_8$ | Me | O | O |
| 195 | Me | O | O | $CH_2CH_2(OCH_2CH_2)_9$ | Me | O | O |
| 196 | Me | O | O | $CH_2CH_2(OCH_2CH_2)_n$ (Mean n = 3) | Me | O | O |
| 197 | Me | O | O | $CH_2CH_2(OCH_2CH_2)_n$ (Mean n = 7) | Me | O | O |
| 198 | Me | O | O | $CH_2CH_2(OCH_2CH_2)_n$ (Mean n = 10) | Me | O | O |
| 199 | Me | O | O | $CH_2CH_2CH_2OCH_2CH_2CH_2$ | Me | O | O |
| 200 | Me | O | O | $CH_2CH_2SCH_2CH_2$ | Me | O | O |
| 201 | Me | O | O | $CH_2CH_2SSCH_2CH_2$ | Me | O | O |
| 202 | Me | O | O | $CH_2CH_2SOCH_2CH_2$ | Me | O | O |
| 203 | Me | O | O | $CH_2CH_2SO_2CH_2CH_2$ | Me | O | O |
| 204 | Me | O | O | $CH_2CH_2CH_2SCH_2CH_2CH_2$ | Me | O | O |
| 205 | Me | O | O | $CH_2CH_2(SCH_2CH_2)_2$ | Me | O | O |
| 206 | Me | O | O | $CH_2CH_2NHCH_2CH_2$ | Me | O | O |
| 207 | Me | O | O | $CH_2CH_2N(Me)CH_2CH_2$ | Me | O | O |
| 208 | Me | O | O | $CH_2CH_2N(Et)CH_2CH_2$ | Me | O | O |
| 209 | Me | O | O | $CH_2CH_2N(Ph)CH_2CH_2$ | Me | O | O |
| 210 | Me | O | O | $CH_2CH_2N(3\text{-}Cl\text{—}Ph)CH_2CH_2$ | Me | O | O |
| 211 | Me | O | O | $CH_2CH_2N(COMe)CH_2CH_2$ | Me | O | O |
| 212 | Me | O | O | $CH_2CH_2N(COEt)CH_2CH_2$ | Me | O | O |
| 213 | Me | O | O | $CH_2CH_2N(COBu\text{-}t)CH_2CH_2$ | Me | O | O |
| 214 | Me | O | O | $CH_2CH_2N(COPh)CH_2CH_2$ | Me | O | O |
| 215 | Me | O | O | $CH_2CH_2N(CO(4\text{-}Cl\text{—}Ph))CH_2CH_2$ | Me | O | O |
| 216 | Me | O | O | $CH_2CH_2N(COQ_3)CH_2CH_2$ | Me | O | O |
| 217 | Me | O | O | $CH_2CH_2N(COOMe)CH_2CH_2$ | Me | O | O |
| 218 | Me | O | O | $CH(Me)CH_2N(COQ_3)CH_2CH(Me)$ | Me | O | O |
| 219 | Me | O | O | $CH_2CH_2N(CH_2CH_2O\text{—}COQ_3)CH_2CH_2$ | Me | O | O |
| 220 | Me | O | O | $CH(Me)CH_2N(CH_2CH_2O\text{—}COQ_3)CH_2CH_2$ | Me | O | O |
| 221 | Me | O | O | $CH_2CH_2\text{—}Q_4\text{—}CH_2CH_2$ | Me | O | O |
| 222 | Me | O | O | $CH_2CH_2(N(COMe)CH_2CH_2)_2$ | Me | O | O |
| 223 | Me | O | O | $CH_2CH_2(N(COEt)CH_2CH_2)_2$ | Me | O | O |

TABLE 1-continued

| No | R$^1$ | X$^1$ | Y$^1$ | R | R$^2$ | X$^2$ | Y$^2$ |
|---|---|---|---|---|---|---|---|
| 224 | Me | O | O | CH$_2$CH$_2$(N(COPh)CH$_2$CH$_2$)$_2$ | Me | O | O |
| 225 | Me | O | O | CH$_2$CH$_2$(N(COQ$_3$)CH$_2$CH$_2$)$_2$ | Me | O | O |
| 226 | Me | O | O | CH$_2$—CO—CH$_2$ | Me | O | O |
| 227 | Me | O | O | CH$_2$—CO—CH(CH)CH$_2$ | Me | O | O |
| 228 | Me | O | O | CH$_2$—CO—CH(O—COQ$_3$)CH$_2$ | Me | O | O |
| 229 | Me | O | O | CH$_2$—CO—CO—CH$_2$ | Me | O | O |
| 230 | Me | O | O | Q$_5$ | Me | O | O |
| 231 | Me | O | O | Q$_6$ | Me | O | O |
| 232 | Me | O | O | Q$_7$ | Me | O | O |
| 233 | Me | O | O | Q$_8$ | Me | O | O |
| 234 | Me | O | O | (CH$_2$)$_2$ | Me | O | S |
| 235 | Me | O | O | (CH$_2$)$_3$ | Me | O | S |
| 236 | Me | O | O | (CH$_2$)$_4$ | Me | O | S |
| 237 | Me | O | O | (CH$_2$)$_5$ | Me | O | S |
| 238 | Me | O | O | (CH$_2$)$_6$ | Me | O | S |
| 239 | Me | O | O | (CH$_2$)$_7$ | Me | O | S |
| 240 | Me | O | O | (CH$_2$)$_8$ | Me | O | S |
| 241 | Me | O | O | CH(Me)CH$_2$ | Me | O | S |
| 242 | Me | O | O | CH(Me)C(Me) | Me | O | S |
| 243 | Me | O | O | CH$_2$CH(O—COQ$_3$)CH$_2$ | Me | O | S |
| 244 | Me | O | O | CH$_2$CH(S—COQ$_3$)CH$_2$ | Me | O | S |
| 245 | Me | O | O | CH$_2$(S—COQ$_3$)CH(S—COQ$_3$)CH$_2$ | Me | O | S |
| 246 | Me | O | O | (CH$_2$)$_2$ | Me | O | N—Me |
| 247 | Me | O | O | (CH$_2$)$_2$ | Me | O | N—Et |
| 248 | Me | O | O | (CH$_2$)$_2$ | Me | O | N—Pr-n |
| 249 | Me | O | O | (CH$_2$)$_2$ | Me | O | N—Pr-i |
| 250 | Me | O | O | (CH$_2$)$_2$ | Me | O | N—Bu-t |
| 251 | Me | O | O | (CH$_2$)$_2$ | Me | O | N—Ph |
| 252 | Me | O | O | (CH$_2$)$_2$ | Me | O | NCH$_2$Ph |
| 253 | Me | O | O | (CH$_2$)$_3$ | Me | O | NH |
| 254 | Me | O | O | (CH$_2$)$_4$ | Me | O | NH |
| 255 | Me | O | O | (CH$_2$)$_5$ | Me | O | NH |
| 256 | Me | O | O | (CH$_2$)$_6$ | Me | O | NH |
| 257 | Me | O | O | (CH$_2$)$_7$ | Me | O | NH |
| 258 | Me | O | O | (CH$_2$)$_8$ | Me | O | NH |
| 259 | Me | O | O | CH$_2$CH(Me) | Me | O | NH |
| 260 | Me | O | O | CH$_2$CH(Et) | Me | O | NH |
| 261 | Me | O | O | CH$_2$CH(Ph) | Me | O | NH |
| 262 | Me | O | O | CH$_2$CH(CH$_2$Ph) | Me | O | NH |
| 263 | Me | O | O | CH$_2$C(Me)$_2$ | Me | O | NH |
| 264 | Me | O | O | CH(Ph)CH$_2$ | Me | O | NH |
| 265 | Me | O | O | CH(3-Q$_3$COOPh)CH$_2$ | Me | O | NH |
| 266 | Me | O | O | CH(4-Q$_3$COOPh)CH$_2$ | Me | O | NH |
| 267 | Me | O | O | CH(Ph)CH$_2$ | Me | O | N—Me |
| 268 | Me | O | O | CH(CH$_2$Ph)CH$_2$ | Me | O | NH |
| 269 | Me | O | O | CH(Ph)CH(Me) | Me | O | NH |
| 270 | Me | O | O | CH(Ph)CH(Me) | Me | O | N—Me |
| 271 | Me | O | O | CH(4-Q$_3$COOPh)CH(Me) | Me | O | N—Me |
| 272 | Me | O | O | Q$_9$ | Me | O | — |
| 273 | Me | O | O | Q$_{10}$ | Me | O | — |
| 274 | Me | O | O | 2,2,6,6-Me$_4$—Q$_{10}$ | Me | O | — |
| 275 | Me | O | O | CH$_2$—Q$_{11}$ | Me | O | — |
| 276 | Me | O | O | CH$_2$—Q$_9$ | Me | O | — |
| 277 | Me | O | O | CH$_2$—Q$_{10}$ | Me | O | — |
| 278 | Me | O | O | CH$_2$CH$_2$—Q$_{11}$ | Me | O | — |
| 279 | Me | O | O | CH$_2$CH$_2$—Q$_9$ | Me | O | — |
| 280 | Me | O | O | CH$_2$CH$_2$—Q$_{10}$ | Me | O | — |
| 281 | Me | O | O | 1-Ph-2 | Me | O | NH |
| 282 | Me | O | O | 1-Ph-3 | Me | O | NH |
| 283 | Me | O | O | 1-Ph-3 | Me | O | NH |
| 284 | Me | O | O | 1-(5-Cl—Ph)-2 | Me | O | NH |
| 285 | Me | O | O | 1-(4-Me—Ph)-2 | Me | O | NH |
| 286 | Me | O | O | 1-(4-t-Bu—Ph)-2 | Me | O | NH |
| 287 | Me | O | O | 1-(2-Me—Ph)-3 | Me | O | NH |
| 288 | Me | O | O | 1-(2,6-Cl$_2$—Ph)-4 | Me | O | NH |
| 289 | Me | O | O | 1-(4-Me—Ph)-3 | Me | O | NH |
| 290 | Me | O | O | 1-(5-O-COQ$_3$—Ph)-4 | Me | O | NH |
| 291 | Me | O | O | (methylnaphthalene structure) | Me | O | NH |

TABLE 1-continued

| No | R¹ | X¹ | Y¹ | R | R² | X² | Y² |
|---|---|---|---|---|---|---|---|
| 292 | Me | O | O | (naphthalene-1,5-diyl) | Me | O | NH |
| 293 | Me | O | O | CH₂-1-(5-Me—Ph)-2 | Me | O | NH |
| 294 | Me | O | S | (CH₂)₂ | Me | O | S |
| 295 | Me | O | S | (CH₂)₃ | Me | O | S |
| 296 | Me | O | S | (CH₂)₄ | Me | O | S |
| 297 | Me | O | S | (CH₂)₅ | Me | O | S |
| 298 | Me | O | S | (CH₂)₆ | Me | O | S |
| 299 | Me | O | S | (CH₂)₇ | Me | O | S |
| 300 | Me | O | S | (CH₂)₈ | Me | O | S |
| 301 | Me | O | S | CH(Me)CH(Me) | Me | O | S |
| 302 | Me | O | S | CH₂CH₂SCH₂CH₂ | Me | O | S |
| 303 | Me | O | S | CH₂CH(COOEt) | Me | O | NH |
| 304 | Me | O | S | 1-Ph-2 | Me | O | NH |
| 305 | Me | O | S | 1-Ph-4 | Me | O | NH |
| 306 | Me | O | NH | (CH₂)₂ | Me | O | NH |
| 307 | Me | O | NH | (CH₂)₂ | Me | O | N—Me |
| 308 | Me | O | NH | (CH₂)₂ | Me | O | N—Et |
| 309 | Me | O | NH | (CH₂)₂ | Me | O | N—Pr-n |
| 310 | Me | O | NH | (CH₂)₂ | Me | D | N—Pr-i |
| 311 | Me | O | NH | (CH₂)₃ | Me | O | NH |
| 312 | Me | O | NH | (CH₂)₃ | Me | O | N—Me |
| 313 | Me | O | NH | (CH₂)₄ | Me | O | N—Pr-n |
| 314 | Me | O | NH | (CH₂)₅ | Me | O | NH |
| 315 | Me | O | NH | (CH₂)₆ | Me | O | NH |
| 316 | Me | O | NH | (CH₂)₇ | Me | O | NH |
| 317 | Me | O | NH | (CH₂)₈ | Me | O | NH |
| 318 | Me | O | NH | (CH₂)₉ | Me | O | NH |
| 319 | Me | O | NH | (CH₂)₁₀ | Me | O | NH |
| 320 | Me | O | NH | (CH₂)₁₁ | Me | O | NH |
| 321 | Me | O | NH | (CH₂)₁₂ | Me | O | NH |
| 322 | Me | O | NH | CH₂CH(Me) | Me | O | NH |
| 323 | Me | O | NH | CH₂C(Me)₂CH₂ | Me | O | NH |
| 324 | Me | O | NH | CH₂CH(COOEt) | Me | O | NH |
| 325 | Me | O | NH | CH₂CH₂CH(COOEt) | Me | O | NH |
| 326 | Me | O | NH | CH₂CH₂CH₂CH(COOEt) | Me | O | NH |
| 327 | Me | O | NH | CH₂CH₂CH₂CH₂CH(COOEt) | Me | O | NH |
| 328 | Me | O | NH | CH₂CH₂OCH₂CH₂ | Me | O | NH |
| 329 | Me | O | NH | CH₂CH₂(OCH₂CH₂)₂ | Me | O | NH |
| 330 | Me | O | NH | CH₂CH₂(OCH₂CH₂)₃ | Me | O | NH |
| 331 | Me | O | NH | CH₂CH₂(OCH₂CH₂)₄ | Me | O | NH |
| 332 | Me | O | NH | CH₂CH₂N(Me)CH₂CH₂ | Me | O | NH |
| 333 | Me | O | NH | CH₂CH₂N(COQ₃)CH₂CH₂ | Me | O | NH |
| 334 | Me | O | NH | CH₂CH₂(N(COQ₃)CH₂CH₂)₂ | Me | O | NH |
| 335 | Me | O | NH | CH₂CH₂(N(COQ₃)CH₂CH₂)₃ | Me | O | NH |
| 336 | Me | O | NH | CH₂CH₂(N(COQ₃)CH₂CH₂)₄ | Me | O | NH |
| 337 | Me | O | NH | CH₂CH₂(N(COQ₃)CH₂CH₂)₅ | Me | O | NH |
| 338 | Me | O | NH | CH₂CH₂(N(COQ₃)CH₂CH₂)₆ | Me | O | NH |
| 339 | Me | O | NH | CH₂CH₂N(COQ₃)—(CH₂)₃ | Me | O | NH |
| 340 | Me | O | NH | CH₂CH₂N(Me)—(CH₂)₃ | Me | O | NH |
| 341 | Me | O | NH | (CH₂)₃N(COQ₃)—(CH₂)₃ | Me | O | NH |
| 342 | Me | O | NH | (CH₂)₄N(COQ₃)—(CH₂)₄ | Me | O | NH |
| 343 | Me | O | NH | (CH₂)₄(N(COQ₃)—(CH₂)₄)₂ | Me | O | NH |
| 344 | Me | O | NH | (CH₂)₄(N(COQ₃)—(CH₂)₄)₃ | Me | O | NH |
| 345 | Me | O | NH | (CH₂)₆N(COQ₃)—(CH₂)₆ | Me | O | NH |
| 346 | Me | O | NH | 1-cyclo-C₆H₁₀-2 | Me | O | NH |
| 347 | Me | O | NH | 1-cyclo-C₆H₁₀-5 | Me | O | NH |
| 348 | Me | O | NH | Q₁₀ | Me | O | — |
| 349 | Me | O | NH | CH₂CH₂Q₁₀ | Me | O | — |
| 350 | Me | O | NH | 1-Ph-2 | Me | O | NH |
| 351 | Me | O | NH | 1-Ph-3 | Me | O | NH |
| 352 | Me | O | NH | 1-Ph-4 | Me | O | NH |
| 353 | Me | O | NH | 1-(4-Cl—Ph)-2 | Me | O | NH |
| 354 | Me | O | NH | 1-(4,5-Me₂—Ph)-2 | Me | O | NH |
| 355 | Me | O | NH | 1-(4-OMe—Ph)-2 | Me | O | NH |
| 356 | Me | O | NH | 1-(2-Me—Ph)-3 | Me | O | NH |
| 357 | Me | O | NH | 1-(4-Me—Ph)-3 | Me | O | NH |
| 358 | Me | O | NH. | 1-(4-OMe—Ph)-3 | Me | O | NH |

TABLE 1-continued

| No | R¹ | X¹ | Y¹ | R | R² | X² | Y² |
|---|---|---|---|---|---|---|---|
| 359 | Me | O | NH | 1-(2-Cl—Ph)-4 | Me | O | NH |
| 360 | Me | O | NH | 1-(2,5-Cl$_2$—Ph)-4 | Me | O | NH |
| 361 | Me | O | NH | 1-(2,6-Cl$_2$—Ph)-4 | Me | O | NH |
| 362 | Me | O | NH | 1-(2-OMe—Ph)-4 | Me | O | NH |
| 363 | Me | O | NH | 1-(1,3,5,6-Me$_4$—Ph)-4 | Me | O | NH |
| 364 | Me | O | N—Me | (CH$_2$)$_2$ | Me | O | N—Me |
| 365 | Me | O | N—Et | (CH$_2$)$_2$ | Me | O | N—Et |
| 366 | Me | O | N—Pr-n | (CH$_2$)$_2$ | Me | O | N—Pr |
| 367 | Me | O | N—Pr-i | (CH$_2$)$_2$ | Me | O | N—Pr |
| 368 | Me | O | — | Q$_4$ | Me | O | — |
| 369 | Me | O | — | Q$_{12}$ | Me | O | — |
| 370 | Me | O | — | Q$_{13}$ | Me | O | — |
| 371 | Me | O | — | Q$_{14}$ | Me | O | — |
| 372 | Et | O | O | (CH$_2$)$_2$ | Et | O | O |
| 373 | Pr-i | O | O | (CH$_2$)$_2$ | Pr-i | O | O |
| 374 | CH$_2$Cl | O | O | (CH$_2$)$_2$ | CH$_2$Cl | O | O |
| 375 | CF$_3$ | O | O | (CH$_2$)$_2$ | CF$_3$ | O | O |
| 376 | Ph | O | O | (CH$_2$)$_2$ | Ph | O | O |
| 377 | 2-Cl—Ph | O | O | (CH$_2$)$_2$ | 2-Cl—Ph | O | O |
| 378 | 3-Cl—Ph | O | O | (CH$_2$)$_2$ | 3-Cl—Ph | O | O |
| 379 | 4-Cl—Ph | O | O | (CH$_2$)$_2$ | 4-Cl—Ph | O | O |
| 380 | 2-Me—Ph | O | O | (CH$_2$)$_2$ | 2-Me—Ph | O | O |
| 381 | 3-Me—Ph | O | O | (CH$_2$)$_2$ | 3-Me—Ph | O | O |
| 382 | 4-Me—Ph | O | O | (CH$_2$)$_2$ | 4-Me—Ph | O | O |
| 383 | 4-t-Bu—Ph | O | O | (CH$_2$)$_2$ | 4-t-Bu—Ph | O | O |
| 384 | 2-CF$_3$—Ph | O | O | (CH$_2$)$_2$ | 2-CF$_3$—Ph | O | O |
| 385 | 4-CF$_3$—Ph | O | O | (CH$_2$)$_2$ | 4-CF$_3$—Ph | O | O |
| 386 | 2,4-Me$_2$—Ph | O | O | (CH$_2$)$_2$ | 2,4-Me$_2$—Ph | O | O |
| 387 | 3,4-Me$_2$—Ph | O | O | (CH$_2$)$_2$ | 3,4-Me$_2$—Ph | O | O |
| 388 | 4-CH—Ph | O | O | (CH$_2$)$_2$ | 4-OH—Ph | O | O |
| 389 | 4-MeO—Ph | O | O | (CH$_2$)$_2$ | 4-MeO—Ph | O | O |
| 390 | 4-CF$_3$O—Ph | O | O | (CH$_2$)$_2$ | 4-CF$_3$O—Ph | O | O |
| 391 | 4-PhO—Ph | O | O | (CH$_2$)$_2$ | 4-PhO—Ph | O | O |
| 392 | 2,4-(MeO)$_2$—Ph | O | O | (CH$_2$)$_2$ | 2,4-(MeO)$_2$—Ph | O | O |
| 393 | 3,4-(MeO)$_2$—Ph | O | O | (CH$_2$)$_2$ | 3,4-(MeO)$_2$—Ph | O | O |
| 394 | 4-COOMe—Ph | O | O | (CH$_2$)$_2$ | 4-COOMe—Ph | O | O |
| 395 | 2,4-Cl$_2$—Ph | O | O | (CH$_2$)$_2$ | 2,4-Cl$_2$—Ph | O | O |
| 396 | 3,4-Cl$_2$—Ph | O | O | (CH$_2$)$_2$ | 3,4-Cl$_2$—Ph | O | O |
| 397 | Q$_{15}$ | O | O | (CH$_2$)$_2$ | Q$_{15}$ | O | O |
| 398 | Q$_{16}$ | O | O | (CH$_2$)$_2$ | Q$_{16}$ | O | O |
| 399 | Q$_{17}$ | O | O | (CH$_2$)$_2$ | Q$_{17}$ | O | O |
| 400 | Q$_{18}$ | O | O | (CH$_2$)$_2$ | Q$_{18}$ | O | O |
| 401 | Q$_{19}$ | O | O | (CH$_2$)$_2$ | Q$_{19}$ | O | O |
| 402 | 6-Cl—Q$_{19}$ | O | O | (CH$_2$)$_2$ | 6-Cl—Q$_{19}$ | O | O |
| 403 | Me | S | NH | (CH$_2$)$_2$ | Me | S | NH |
| 404 | Me | S | NH | (CH$_2$)$_3$ | Me | S | NH |
| 405 | Me | S | NH | (CH$_2$)$_4$ | Me | S | NH |
| 406 | Me | S | NH | 1-Ph-2 | Me | S | NH |
| 407 | Me | S | NH | 1-Ph-3 | Me | S | NH |
| 408 | Me | S | NH | 1-Ph-4 | Me | S | NH |

Table 1 shows that, for example, R of compound No. 141 is "1-cyclo-C$_5$H$_8$-2" which means Y$^1$ and Y$^2$ are linked to the 1-position and 2-potition, respectively, of a cyclopentyl ring. It is similarly shown that R of compound No. 154 is "1-Ph-2" which means Y$^1$ and Y$^2$ are linked to the 1-position and 2-position, respectively, of the phenyl ring of 1,2-phenylene group.

Table 2 lists characteristic properties of the typical compounds shown in Table 1.

TABLE 2

| Compound No. | Property |
|---|---|
| 2 | m.p. 54° C. |
| 4 | m.p. 91° C. |
| 21 | Paste [NMR (CDCl$_3$/TMS, δ value (ppm))] 1.47(d, 6.6Hz, 3H), 2.94(s, 6H), 4.40(dd, 6.7Hz, 12.1Hz, 1H), 4.60(dd, 3.2Hz, 12.1Hz, 1H), 5.4–5.6(m, 1H) |

TABLE 2-continued

| Compound No. | Property |
|---|---|
| 35 | nD 1.5722 (22° C.) |
| 82 | nD 1.5403 (22° C.) |
| 95 | m.p. 95° C. |
| 96 | m.p. 190° C. |
| 106 | Paste [NMR (CDCl$_3$/TMS, δ value (ppm))] 2.97(s, 9H), 4.60(dd, 2H), 4.75(dd, 2H), 5.65–5.80(m, 1H). |
| 140 | m.p. 79° C. |
| 156 | m.p. 205° C. |
| 166 | m.p. 184° C. |
| 176 | m.p. 149° C. |
| 184 | m.p. 122° C. |
| 187 | nD 1.5416 (26° C.) |
| 188 | nD 1.5325 (26° C.) |
| 196 | nD 1.5222 (26° C.) |
| 197 | Paste [NMR (CDCl$_3$/TMS, δ value (ppm))] 2.95(s, 6H), 3.50–3.70(m, ≈24H), 3.76–3.82(m, 4H), 4.45–4.52(m, 4H). |

TABLE 2-continued

| Compound No. | Property |
|---|---|
| 198 | Paste [NMR (CDCl$_3$/TMS, δ value (ppm))] 2.97(s, 6H), 3.57–3.75(m, ≈38H), 3.76–3.83(m, 4H), 4.45–4.53(m, 4H). |
| 214 | nD 1.5627 (21° C.) |
| 219 | Paste [NMR (CDCl$_3$/TMS, δ value (ppm))] 2.92(s, 69H), 2.96–3.06(m, 6H), 4.34–4.45(m, 6H). |
| 281 | m.p. 112° C. |
| 282 | m.p. 152° C. |
| 283 | m.p. 167° C. |
| 288 | m.p. 164° C. |
| 306 | m.p. 149° C. |
| 350 | m.p. 189° C. |
| 351 | m.p. 210° C. |
| 352 | m.p. 260° C. |

The bis-thiadiazole derivatives of the general formula (I) or salts thereof according to the present invention are useful for agricultural and horticultural disease control. For example, these compounds have a very high controlling effect against various diseases, for instance, rice blast (*Pyricularia oryzae*), rice sheath blight (*Rhizoctonia solani*), rice helminthosporium leaf spot (*Cochiobolus miyabeanus*), powdery mildew of various host plants such as powdery mildew of barley and wheat (*Erysiphe graminis*), oats crown rust (*Puccinia coronata*) and rust of other plants, tomato late blight (*Phytophthora infestans*) and late blight or *Phytophthora rots* of other plants, downy mildew of various plants such as cucumber downy mildew (*Pseudoperonospora cubensis*) and grape downy mildew (*Plasmopara viticola*), apple scab (*Venturia inaequalis*), apple alternaria leaf spot (*Alternaria mali*), pear black spot (*Alternaria kikuchiana*), citrus melanose (*Diaporthe citri*), bacterial diseases including Pseudomonas diseases such as cucumber bacterial blight (*Pseudomonas syringae* pv. *lachrymans*) and tomato bacterial wilt (*Pseudomonas solanacearum*), Xanthomonas diseases such as cabbage black rot (*Xanthomonas campestris*), rice bacterial leaf blight (*Xanthomonas oryzae*) and citrus canker (*Xanthomonas citri*) and Erwinia diseases such as cabbage bacterial soft rot (*Erwinia carotovora*), and viral diseases such as tobacco mosaic (*Tobacco mosaic* virus).

The agrohorticultural disease controller containing the bis-thiadiazole derivative of general formula (I) or salts thereof as an active ingredient according to the present invention exhibits a marked controlling effect against the above-exemplified diseases which damage paddy field crops, upland field crops, fruit trees, vegetables, other crop plants, flowers, ornamental plants, and the like. Accordingly, the desired effects of the agrohorticultural disease controller of the present invention can be obtained by applying the disease controller to the paddy field water, stalks and leaves or soil of the paddy field, upland field, fruit trees, vegetables, other crops, flowers and ornamental plants at a season at which the diseases are expected to occur, before their occurrence or at the time when their occurrence has been confirmed.

The agrohorticultural disease controller of the present invention is generally put to use after being prepared into a conveniently usable form according to an ordinary manner for preparation of pesticides.

That is, the bis-thiadiazole derivative represented by the general formula (I) or a salt thereof according to the present invention and, optionally, an adjuvant are blended with an appropriate inert carrier in a proper proportion, prepared into a suitable preparation form such as suspension, emulsifiable concentrate, soluble concentrate, wettable powder, granule, dust, tablet, etc. and put to use through dissolution, separation, suspension, mixing, impregnation, adsorption or sticking.

The inert carrier used in the present invention may be either solid or liquid. As the material usable as solid carrier, there can be exemplified soybean flour, cereal flour, wood flour, bark flour, saw dust, powdered tobacco stalks, powdered walnut shells, bran, powdered cellulose, extraction residue of vegetables, powdered synthetic polymers of synthetic resins and the like, clays such as kaolin, bentonite, acid clay and the like, talcs such as talc, pyrophyllite and the like, silica powders and flakes such as diatomaceous earth, siliceous sand, mica, white carbon (namely, synthetic, high-dispersion silicic acid, also called finely divided hydrated silica or hydrated silicic acid, some of the commercially available products thereof contain calcium silicate as the major component), activated carbon, powdered sulfur, pumice, calcined diatomaceous earth, crushed brick, fly ash, sand, inorganic mineral powders such as calcium carbonate, calcium phosphate and the like, chemical fertilizers such as ammonium sulfate, ammonium phosphate, ammonium nitrate, urea, ammonium chloride and the like, and compost. These carriers may be used alone or as a mixture thereof.

The material constituting the liquid carrier is selected from materials having a dissolving ability in themselves and materials which have no dissolving ability in themselves but can disperse the active ingredient compound by aid of an adjuvant. The following are typical examples of the liquid carrier material, which can be used either alone or in the form of a mixture: water; alcohols such as methanol, ethanol, isopropanol, butanol, ethylene glycol and the like; ketones such as acetone, methyl ethyl ketone, methyl isobutyl ketone, diisobutyl ketone, cyclohexanone and the like; ethers such as ethyl ether, dioxane, cellosolve, dipropyl ether, tetrahydrofuran and the like; aliphatic hydrocarbons such as kerosene, mineral oils and the like; aromatic hydrocarbons such as benzene, toluene, xylene, solvent naphtha, alkylnaphthalene and the like; halogenated hydrocarbons such as dichloroethene, chloroform, carbon tetrachloride, chlorobenzene and the like; esters such as ethyl acetate, diisopropyl phthalate, dibutyl phthalate, dioctyl phthalate and the like; amides such as dimethylformamide, diethylformamide, dimethylacetamide and the like; nitriles such as acetonitrile and the like; dimethyl sulfoxide; etc.

As the adjuvant, the following can be referred to as typical ones. These adjuvants are used depending upon purposes, either alone or in combination of two or more in some cases. It is also possible to use no adjuvant at all, in some cases.

A surfactant is used for the purpose of emulsifying, dispersing, solubilizing and/or wetting an active ingredient. As the surfactant, there can be exemplified polyoxyethylene alkyl ethers, polyoxyethylene alkylaryl ethers, polyoxyethylene higher fatty acid esters, polyoxyethylene resin acid esters, polyoxyethylene sorbitan monolaurate, polyoxyethylene sorbitan monooleate, alkylarylsulfonates, naphthalenesulfonic acid condensates, ligninsulfonic acid salts, higher alcohol sulfuric esters, etc.

The following adjuvants can also be used for the purpose of stabilizing, tackifying and/or binding the dispersion of active ingredient compound: casein, gelatin, starch, methyl cellulose, carboxymethyl cellulose, gum arabic, polyvinyl alcohol, turpentine, bran oil, bentonite, ligninsulfonic acid salts and the like.

Further, wax, stearic acid salts, alkyl phosphates and the like may be used as an adjuvant for the purpose of improving flowability of a solid product.

Further, naphthalenesulfonic acid condensates, polycondensed phosphoric acid salts and the like may also be used as a peptizer for dispersible products.

Adjuvants such as silicone oils may also be used as a defoaming agent.

The content of the active ingredient may be increased or decreased according to the need. For example, in dusts and granules, the suitable content thereof is from 0.01 to 50% by weight. In emulsifiable concentrates and wettable powders, too, the suitable content thereof is from 0.01 to 50% by weight.

For controlling various diseases, the agrohorticultural disease controller of the present invention itself or its appropriate dilution or suspension in water or the like is applied to a crop on which the diseases are expected to occur or a site where occurrence of the diseases is undesirable, in an amount effective for disease control. For example, for controlling the diseases of paddy rice, said disease controller can be used by a method such as direct application to regular paddy field, application to a rice nursery bed, dressing of seeds for direct sowing to flooded paddy field, seed disinfection, etc. For controlling the diseases of barley, wheat, oat or the like, the disease controller of the present invention is applied to stalks and leaves or used for soil treatment where the disease controller is absorbed from the roots.

The application amount of the agrohorticultural disease controller of the present invention may vary depending on various factors including purpose of application, objective disease, state of plant growth, tendency of prevalence of the disease, weather, environmental conditions, preparation form, method of application, site of application, time of application, etc. The application amount, however, should be properly chosen in the range of from 0.1 g to 10 kg per 10 ares as expressed in terms of amount of active ingredient, depending on purposes.

In order to expand the spectrum of controllable diseases and the time period of effective application or to reduce the dosage, it is also possible to use the disease controller of the present invention in the form of a mixture with other agrohorticultural disease controllers.

Next, typical examples, formulation examples and test examples of the present invention are presented below. The present invention is by no means limited by these examples.

EXAMPLE 1

Production of ethylene-bis(4-methyl-1,2,3-thiadiazole-5-carboxylate) (Compound No. 2)

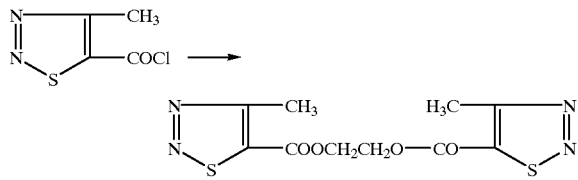

In 30 ml of tetrahydrofuran was dissolved 0.80 g (4.9 mmol) of 4-methyl-1,2,3-thiadiazole-5-carbonyl chloride, to which was then added 0.12 g (2.0 mmol) of ethylene glycol. While stirring the mixture at room temperature, 0.50 ml of triethylamine was dropwise added thereto and stirred at room temperature for 4 hours. After the reaction was completed, ethyl acetate was added to the reaction mixture, the organic layer was washed successively with aqueous solution of hydrochloric acid and aqueous solution of sodium hydrogen carbonate, dried on anhydrous magnesium sulfate, and concentrated under reduced pressure. The residue was purified by silica gel column chromatography using 2:1 mixture of n-hexane and ethyl acetate. Thus, the objective compound was obtained in a yield of 0.34 g.

Property: m.p. 54° C.

Yield: 56%

EXAMPLE 2

Production of 2-butynylene-bis(4-methyl-1,2,3-thiadiazole-5-carboxylate) (Compound No. 140)

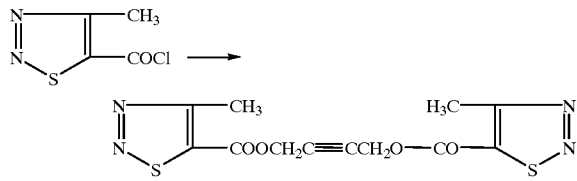

In 30 ml of tetrahydrofuran was dissolved 0.70 g (4.3 mmol) of 4-methyl-1,2,3-thiadiazole-5-carbonyl chloride, to which was added 0.15 g (1.7 mmol) of 2-butyne-1,4-diol. While stirring the mixture at room temperature, 0.50 ml of triethylamine was dropwise added and stirred at room temperature for 4 hours. After the reaction was completed, ethyl acetate was added to the reaction mixture, the organic layer was washed successively with aqueous solution of hydrochloric acid and aqueous solution of sodium hydrogen carbonate and dried on anhydrous magnesium sulfate, and concentrated under reduced pressure. The residue was purified by silica gel column chromatography using 2:1 mixture of n-hexane and ethyl acetate. Thus, the objective compound was obtained in a yield of 0.34 g.

Property: m.p. 79° C.

Yield: 61%

EXAMPLE 3

Production of p-phenylene-bis(4-methyl-1,2,3-thiadiazole-5-carboxylate) (Compound No. 156)

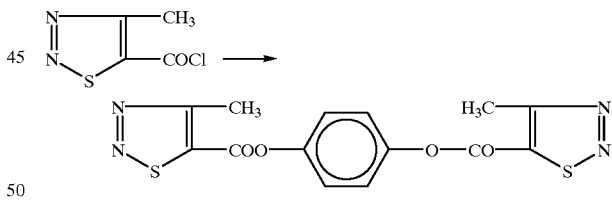

In 30 ml of tetrahydrofuran was dissolved 1.0 g (6.2 mmol) of 4-methyl-1,2,3-thiadiazole-5-carbonyl chloride, to which was then added 0.27 g (2.5 mmol) of p-hydroquinone. While stirring the mixture at room temperature, 0.50 ml of triethylamine was dropwise added thereto and stirred at room temperature for 4 hours. After the reaction was completed, ethyl acetate was added to the reaction mixture, and the organic layer was washed successively with aqueous solution of hydrochloric acid and aqueous solution of sodium hydrogen carbonate and dried on anhydrous magnesium sulfate. The dried organic solution was concentrated under reduced pressure, and the residue was purified by silica gel column chromatography using 2:1 mixture of n-hexane and ethyl acetate. Thus, the objective compound was obtained in a yield of 0.30 g.

Property: m.p. 205° C.

Yield: 34%

EXAMPLE 4

Production of p-α,α-xylylene-bis(4-methyl-1,2,3-thiadiazole-5-carboxylate) (Compound No. 184)

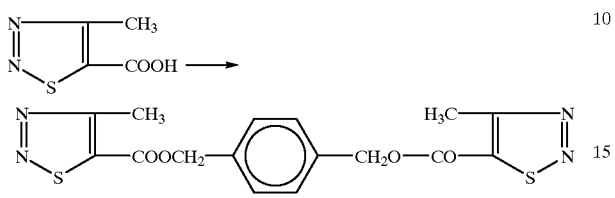

In 30 ml of acetonitrile was dissolved 0.50 g (3.5 mmol) of 4-methyl-1,2,3-thiadiazole-5-carboxylic acid, to which were added 0.37 g (1.4 mmol) of p-α,α-xylylene dibromide and 0.50 g (3.6 mmol) of anhydrous potassium carbonate. The resulting mixture was heated under reflux for 4 hours. After the reaction was completed, ethyl acetate was added to the reaction mixture, the organic layer was dried over anhydrous magnesium sulfate and concentrated under reduced pressure, and the residue was purified by silica gel column chromatography using 4:1 mixture of n-hexane and ethyl acetate. Thus, the objective compound was obtained in a yield of 0.15 g.

Property: m.p. 122° C.

Yield: 27%

EXAMPLE 5

Production of polyoxyethylene (mean value of n=4)-bis(4-methyl-1,2,3-thiadiazole-5-carboxylate) (Compound No. 196)

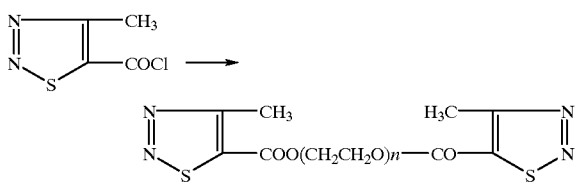

In 30 ml of tetrahydrofuran was dissolved 1.60 g (10 mmol) of 4-methyl-1,2,3-thiadiazole-5-carbonyl chloride, to which was added 0.50 g (2.5 mmol) of PEG 200 (polyethylene glycol). While stirring the resulting mixture at room temperature, 0.50 ml of triethylamine was dropwise added thereto and stirred at room temperature for 4 hours. After the reaction was completed, ethyl acetate was added to the reaction mixture, the organic layer was washed successively with aqueous solution of hydrochloric acid and aqueous solution of sodium hydrogen carbonate, dried over anhydrous magnesium sulfate and concentrated under reduced pressure, and the residue was purified by silica gel column chromatography using 1:1 mixture of n-hexane and ethyl acetate. Thus, the objective compound was obtained in a yield of 0.59 g.

Property: nD 1.5222 (26° C.)

Yield: 52%

EXAMPLE 6

Production of 2,6-dichloro-4-(4-methyl-1,2,3-thiadiazol-5-ylcarbonylamino)-phenyl 4-methyl-1,2,3-thiadiazole-5-carboxylate (Compound No. 288)

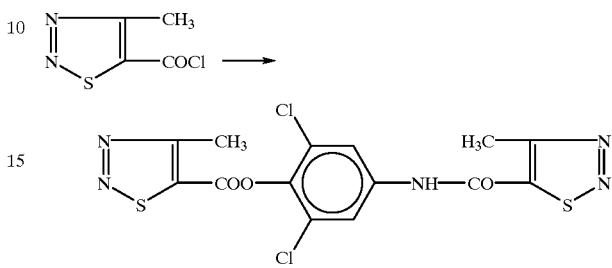

In 30 ml of tetrahydrofuran was dissolved 1.0 g (4.1 mmol) of 4-methyl-1,2,3-thiadiazole-5-carbonyl chloride, to which was added 0.20 g (2.0 mmol) of 2,6-dichloro-p-aminophenol. While stirring the mixture at room temperature, 1.0 ml of triethylamine was dropwise added and stirred at room temperature for 4 hours. After the reaction was completed, ethyl acetate was added to the reaction mixture, and the organic layer was washed successively with aqueous solution of hydrochloric acid and aqueous solution of sodium hydrogen carbonate, dried over anhydrous magnesium sulfate, and concentrated under reduced pressure. Thus, the objective compound was obtained in a yield of 0.62 g.

Property: m.p. 260° C.

Yield: 33%

EXAMPLE 7

Production of N,N'-p-phenylenebis(4-methyl-1,2,3-thiadiazole-5-carboxamide) (Compound No. 352)

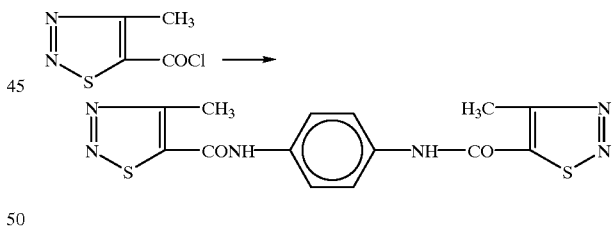

In 30 ml of tetrahydrofuran was dissolved 0.80 g (4.9 mmol) of 4-methyl-1,2,3-thiadiazole-5-carbonyl chloride, to which was added 0.20 g (1.9 mmol) of p-phenylenediamine. While stirring the mixture at room temperature, 1.0 ml of triethylamine was dropwise added and stirred at room temperature for 4 hours. After the reaction was completed, ethyl acetate was added to the reaction mixture, and the organic layer was washed successively with aqueous solution of hydrochloric acid and aqueous solution of sodium hydrogen carbonate, dried over anhydrous magnesium sulfate, and concentrated under reduced pressure. Thus, the objective compound was obtained in a yield of 0.62 g.

Property: m.p. 164° C.

Yield: 73%

Next, typical examples and test examples of the present invention are presented below.

In the formulation examples, the term parts means parts by weight.

Formulation Example 1

| The compound of Table 1 | 50 parts |
| Xylene | 40 parts |
| Mixture of polyoxyethylene nonylphenyl ether and calcium alkylbenzenesulfonate | 10 parts |

The ingredients mentioned above are uniformly mixed and dissolved together to prepare an emulsifiable concentrate.

Formulation Example 2

| The compound of Table 1 | 3 parts |
| Clay powder | 82 parts |
| Diatomaceous earth powder | 15 parts |

The ingredients mentioned above are uniformly mixed and pulverized to prepare a dust.

Formulation Example 3

| The compound of Table 1 | 5 parts |
| Powdered mixture of bentonite and clay | 90 parts |
| Calcium ligninsulfonate | 5 parts |

The ingredients mentioned above are uniformly mixed together, kneaded together with an appropriate quantity of water, granulated and dried to prepare a granular composition.

Formulation Example 4

| The compound of Table 1 | 20 parts |
| Kaolinite and synthetic high-disperse silicic acid | 75 parts |
| Mixture of polyoxyethylene nonylphenyl ether and calcium alkylbenzenesulfonate | 5 parts |

The ingredients mentioned above are uniformly mixed and pulverized to prepare a wettable powder.

Test Example 1

Rice Blast-controlling Test by Submerged Application

A chemical agent containing the compound shown in Table 1 as an active ingredient was applied to paddy rice plants of the 5- to 6-leaved stage, cultivated in 1/10000 are pots, by the method of submerged application at a dosage of 200 g/10 a as expressed in terms of active ingredient. After standing in a greenhouse for a week, the plants were inoculated with a spore suspension of rice blast fungus (*Pyricularia oryzae*) by the method of spraying.

After the inoculation, the plants were allowed to stand in a moist chamber for one day and then in a greenhouse for 6 days to cause the disease sufficiently. Then, lesions on each leaf were counted and compared with those in the untreated plot, from which the controlling degree was calculated, whereby the effect was judged according to the following criterion:

| Effect | Controlling degree (%) |
|---|---|
| A | 100–95 |
| B | 94–85 |
| C | 84–60 |
| D | 59–0 |

The results of the above test demonstrate that the compounds listed in Table 1 were found to have a marked blast-controlling activity. Of these compounds, the following were rated C or higher: Compound Nos. 2, 82, 96, 106, 140, 156, 166, 176, 187, 188, 196, 219, 281, 282, 283, 288, 351 and 352; among which Compound Nos. 2, 106, 156, 166, 188, 196, 219, 282, 283, 288, 351 and 352 exhibit so high a controlling effect as rated A.

What is claimed is:

1. A bis-thiadiazole derivative represented by the following general formula (I) or a salt thereof:

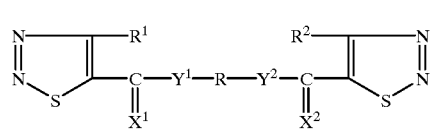

(I)

wherein $R^1$ and $R^2$, same or different, represent hydrogen atom, $C_1$–$C_8$ alkyl group, halo $C_1$–$C_4$ alkyl group, phenyl group, substituted phenyl group having 1 to 5 same or different substituents selected from the group consisting of halogen atom, nitro group, cyano group, hydroxyl group, mercapto group, $C_1$–$C_4$ alkyl group, halo $C_1$–$C_4$ alkyl group, $C_1$–$C_4$ alkoxy group, halo $C_1$–$C_4$ alkoxy group, $C_1$–$C_4$ alkylthio group, halo $C_1$–$C_4$ alkylthio group, amino group and substituted amino group having 1 or 2 same or different substituents selected from the group consisting of $C_1$–$C_4$ alkyl and phenyl groups, 5- or 6-membered hererocycle containing 1 to 3 same or different hetero atoms selected from the group consisting of oxygen atom, sulfur atom and nitrogen atom, or substituted 5- or 6 membered heterocycle containing 1 to 3 same or different hetero atoms selected from the group consisting of oxygen atom, sulfur atom and nitrogen atom and having 1 to 5 same or different substituents selected from the group consisting of halogen atom, nitro group, cyano group, hydroxyl group, mercapto group, $C_1$–$C_4$ alkyl group, halo $C_1$–$C_4$ alkyl group, $C_1$–$C_4$ alkoxy group, halo $C_1$–$C_4$ alkoxy group, $C_1$–$C_4$ alkylthio group, halo $C_1$–$C_4$ alkylthio group, amino group and substituted amino group having 1 or 2 same or different substituents selected from the group consisting of $C_1$–$C_4$ alkyl and phenyl groups;

$X^1$ and $X^2$, same or different, represent oxygen atom or sulfur atom;

$Y^1$ and $Y^2$, same or different, represent oxygen atom, sulfur atom or

—N($R^3$)— in which $R^3$ is as defined later; and

R represents $C_0$–$C_{30}$ alkylene group, an alkylene group of the following formula:

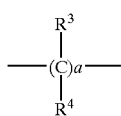

in which $R^3$ and $R^4$, same or different, represent hydrogen atom, halogen atom, hydroxyl group, nitro group, cyano group, $C_1$–$C_4$ alkyl group, halo $C_1$–$C_4$ alkyl group, $C_1$–$C_4$ alkoxy group, halo $C_1$–$C_4$ alkoxy group, $C_1$–$C_4$ alkylthio group, $C_1$–$C_4$ alkylsulfinyl group, $C_1$–$C_4$ alkylsulfonyl group, hydroxy $C_1$–$C_4$ alkyl group, $C_1$–$C_4$ alkoxy $C_1$–$C_4$ alkyl group, $C_1$–$C_4$ alkoxycarbonyl group, amino group, substituted amino group having 1 or 2 same or different substituents selected from the group consisting of $C_1$–$C_4$ alkyl group, phenyl group and substituted phenyl groups having 1 to 5 same or different substituents selected from the group consisting of halogen atom, nitro group, cyano group, hydroxyl group, mercapto group, $C_1$–$C_4$ alkyl group, halo $C_1$–$C_4$ alkyl group, $C_1$–$C_4$ alkoxy group, halo $C_1$–$C_4$ alkoxy group, $C_1$–$C_4$ alkylthio group, halo $C_1$–$C_4$ alkylthio group, amino group and substituted amino group having 1 or 2 same or different substituents selected from the group consisting of $C_1$–$C_4$ alkyl and phenyl groups, amino $C_1$–$C_4$ alkyl group, substituted amino $C_1$–$C_4$ alkyl group having 1 or 2 same or different substituents selected from substituted phenyl groups having 1 to 5 same or different substituents selected from the group consisting of halogen atom, nitro group, cyano group, hydroxyl group, mercapto group, $C_1$–$C_4$ alkyl group, halo $C_1$–$C_4$ alkyl group, $C_1$–$C_4$ alkoxy group, halo $C_1$–$C_4$ alkoxy group, $C_1$–$C_4$ alkylthio group, halo $C_1$–$C_4$ alkylthio group, amino group and substituted amino group having 1 or 2 same or different substituents selected from the group consisting of $C_1$–$C_4$ alkyl and phenyl groups, phenyl group, substituted phenyl group having 1 to 5 same or different substituents selected from the group consisting of halogen atom, nitro group, cyano group, hydroxyl group, mercapto group, $C_1$–$C_4$ alkyl group, halo $C_1$–$C_4$ alkyl group, $C_1$–$C_4$ alkoxy group, halo $C_1$–$C_4$ alkoxy group, $C_1$–$C_4$ alkylthio group, halo $C_1$–$C_4$ alkylthio group, amino group and substituted amino group having 1 or 2 same or different substituents selected from the group consisting of $C_1$–$C_4$ alkyl and phenyl groups, phenyl $C_1$–$C_4$ alkyl group, substituted phenyl $C_1$–$C_4$ alkyl group having, on the ring thereof, 1 to 5 same or different substituents selected from the group consisting of halogen atom, nitro group, cyano group, hydroxyl group, mercapto group, $C_1$–$C_4$ alkyl group, halo $C_1$–$C_4$ alkyl group, $C_1$–$C_4$ alkoxy group, halo $C_1$–$C_4$ alkoxy group, $C_1$–$C_4$ alkylthio group, halo $C_1$–$C_4$ alkylthio group, amino group and substituted amino group having 1 or 2 same or different substituents selected from the group consisting of $C_1$–$C_4$ alkyl and phenyl groups, phenoxy group, substituted phenoxy group having, on the ring thereof, 1 to 5 same or different substituents selected from the group consisting of halogen atom, nitro group, cyano group, hydroxyl group, mercapto group, $C_1$–$C_4$ alkyl group, halo $C_1$–$C_4$ alkyl group, $C_1$–$C_4$ alkoxy group, halo $C_1$–$C_4$ alkoxy group, $C_1$–$C_4$ alkylthio group, halo $C_1$–$C_4$ alkylthio group, amino group and substituted amino group having 1 or 2 same or different substituents selected from the group consisting of $C_1$–$C_4$ alkyl and phenyl groups, phenoxy $C_1$–$C_4$ alkyl group, substituted phenoxy $C_1$–$C_4$ alkyl group having, on the ring thereof, 1 to 5 same or different substituents selected from the group consisting of halogen atom, nitro group, cyano group, hydroxyl group, mercapto group, $C_1$–$C_4$ alkyl group, halo $C_1$–$C_4$ alkyl group, $C_1$–$C_4$ alkoxy group, halo $C_1$–$C_4$ alkoxy group, $C_1$–$C_4$ alkylthio group, halo $C_1$–$C_4$ alkylthio group, amino group and substituted amino group having 1 or 2 same or different substituents selected from the group consisting of $C_1$–$C_4$ alkyl and phenyl groups, 5- or 6-membered heterocycle containing 1 to 3 same or different hetero atoms selected from the group consisting of oxygen atom, sulfur atom and nitrogen atom, substituted 5 or 6-membered heterocycle containing 1 to 3 same or different hetero atoms selected from the group consisting of oxygen atom, sulfur atom and nitrogen atom and having 1 to 4 same or different substituents selected from the group consisting of halogen atom, nitro group, cyano group, hydroxyl group, mercapto group, $C_1$–$C_4$ alkyl group, halo $C_1$–$C_4$ alkyl group, $C_1$–$C_4$ alkoxy group, halo $C_1$–$C_4$ alkoxy group, $C_1$–$C_4$ alkylthio group, halo $C_1$–$C_4$ alkylthio group, amino group and substituted amino group having 1 or 2 same or different substituents selected from the group consisting of $C_1$–$C_4$ alkyl and phenyl groups, 5- or 6-membered heterocycle $C_1$–$C_4$ alkyl group containing 1 to 3 same or different hetero atoms selected from the group consisting of oxygen atom, sulfur atom and nitrogen atom, substituted 5- or 6-membered hetero cycle $C_1$–$C_4$ alkyl group containing 1 to 3 same or different hetero atoms selected from the group consisting of oxygen atom, sulfur atom and nitrogen atom and having 1 to 4 same or different substituents selected from the group consisting of halogen atom, nitro group, cyano group, hydroxyl group, mercapto group, $C_1$–$C_4$ alkyl group, halo $C_1$–$C_4$ alkyl group, $C_1$–$C_4$ alkoxy group, halo $C_1$–$C_4$ alkoxy group, $C_1$–$C_4$ alkylthio group, halo $C_1$–$C_4$ alkylthio group, amino group and substituted amino group having 1 or 2 same or different substituents selected from the group consisting of $C_1$–$C_4$ alkyl and phenyl groups, or a group of $$\text{—}(R^6)m\text{—}(Y^3)p\text{—}\underset{X^3}{\overset{\|}{C}}\text{—}R^7$$

(wherein $R^6$ represents $C_1$–$C_6$ alkylene group, substituted $C_1$–$C_6$ alkylene group substituted by one or more same or different halogen atoms or $C_1$–$C_4$ alkyl groups, or $C_1$–$C_6$ alkylene group which may be intercepted by

—O—,

—S(O)$_n$— in which n is an integer of 0–2, or

—N($R^8$)— in which $R^8$ represents hydrogen atom, halogen atom, $C_1$–$C_4$ alkyl group, halo $C_1$–$C_4$ alkyl group, $C_1$–$C_4$ alkoxycarbonyl group, phenyl group, substituted phenyl group having 1 to 5 same or different substituents selected from the group consisting of halogen atom, nitro group, cyano group, hydroxyl group, mercapto group, $C_1$–$C_4$ alkyl group, halo $C_1$–$C_4$ alkyl group, $C_1$–$C_4$ alkoxy group, halo $C_1$–$C_4$ alkoxy group, $C_1$–$C_4$ alkylthio group, halo $C_1$–$C_4$ alkylthio group, amino group and substituted amino group having 1 or 2 same or different substituents selected from the group consisting of $C_1$–$C_4$ alkyl and phenyl groups, phenyl $C_1$–$C_4$ alkyl group, substituted phenyl $C_1$–$C_4$ alkyl group having 1 to 5 same or different substituents selected from the group consisting of halogen atom, nitro group, cyano group, hydroxyl group, mercapto group, $C_1$–$C_4$ alkyl group, halo $C_1$–$C_4$ alkyl group, $C_1$–$C_4$ alkoxy group, halo $C_1$–$C_4$ alkoxy group, $C_1$–$C_4$ alkylthio group, halo $C_1$–$C_4$ alkylthio group, amino group and substituted amino group having 1 or 2 same or different substituents selected from the group consisting of $C_1$–$C_4$ alkyl and phenyl groups, or

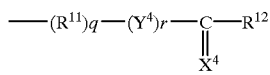

(wherein $R^{11}$ represents $C_1$–$C_6$ alkylene group or substituted $C_1$–$C_6$ alkylene group having one or more substituents selected from the group consisting of halogen atom and $C_1$–$C_4$ alkyl group;

$R^{12}$ represents hydrogen atom, $C_1$–$C_8$ alkyl group, halo $C_1$–$C_4$ alkyl group, phenyl group, substituted phenyl group having 1 to 5 same or different substituents selected from the group consisting of halogen atom, nitro group, cyano group, hydroxyl group, mercapto group, $C_1$–$C_4$ alkyl group, halo $C_1$–$C_4$ alkyl group, $C_1$–$C_4$ alkoxy group, halo $C_1$–$C_4$ alkoxy group, $C_1$–$C_4$ alkylthio group, halo $C_1$–$C_4$ alkylthio group, amino group and substituted amino group having 1 or 2 same or different substituents selected from the group consisting of $C_1$–$C_4$ alkyl and phenyl groups, 5- or 6-membered heterocycle containing 1 to 3 same or different hetero atoms selected from the group consisting of oxygen atom, sulfur atom and nitrogen atom, or substituted 5- or 6-membered heterocycle containing 1 to 3 same or different hetero atoms selected from the group consisting of oxygen atom, sulfur atom and nitrogen atom and having 1 to 4 same or different substituents selected from the group consisting of halogen atom, nitro group, cyano group, hydroxyl group, mercapto group, $C_1$–$C_4$ alkyl group, halo $C_1$–$C_4$ alkyl group, $C_1$–$C_4$ alkoxy group, halo $C_1$–$C_4$ alkoxy group, $C_1$–$C_4$ alkylthio group, halo $C_1$–$C_4$ alkylthio group, amino group and substituted amino group having 1 or 2 same or different substituents selected from the group consisting of $C_1$–$C_4$ alkyl and phenyl groups;

$Y^4$ represents
—O—,
—S— or
—N($R^{13}$)— in which $R^{13}$ represents hydrogen atom or $C_1$–$C_4$ alkyl group;

$X^4$ represents oxygen atom or sulfur atom;
q represents an integer of 0 to 1; and
r represents an integer of 0 to 1);

$R^7$ represents hydrogen atom, $C_1$–$C_8$ alkyl group, halo $C_1$–$C_8$ alkyl group, phenyl group, substituted phenyl group having 1 to 5 same or different substituents selected from the group consisting of halogen atom, nitro group, cyano group, hydroxyl group, mercapto group, $C_1$–$C_4$ alkyl group, halo $C_1$–$C_4$ alkyl group, $C_1$–$C_4$ alkoxy group, halo $C_1$–$C_4$ alkoxy group, $C_1$–$C_4$ alkylthio group, halo $C_1$–$C_4$ alkylthio group, amino group and substituted amino group having 1 or 2 same or different substituents selected from the group consisting of $C_1$–$C_4$ alkyl and phenyl groups, phenyl $C_1$–$C_4$ alkyl group, substituted phenyl $C_1$–$C_4$ alkyl group having, on the ring thereof, 1 to 5 same or different substituents selected from the group consisting of halogen atom, nitro group, cyano group, hydroxyl group, mercapto group, $C_1$–$C_4$ alkyl group, halo $C_1$–$C_4$ alkyl group, $C_1$–$C_4$ alkoxy group, halo $C_1$–$C_4$ alkoxy group, $C_1$–$C_4$ alkylthio group, halo $C_1$–$C_4$ alkylthio group, amino group and substituted amino group having 1 or 2 same or different substituents selected from the group consisting of $C_1$–$C_4$ alkyl and phenyl groups, 5- or 6-membered heterocycle containing 1 to 3 same or different hetero atoms selected from the group consisting of oxygen atom, sulfur atom and nitrogen atom, or substituted 5 or 6-membered heterocycle containing 1 to 3 same or different hetero atoms selected from the group consisting of oxygen atom, sulfur atom and nitrogen atom and having, on the ring thereof, 1 to 5 same or different substituents selected from the group consisting of halogen atom, nitro group, cyano group, hydroxyl group, mercapto group, $C_1$–$C_4$ alkyl group, halo $C_1$–$C_4$ alkyl group, $C_1$–$C_4$ alkoxy group, halo $C_1$–$C_4$ alkoxy group, $C_1$–$C_4$ alkylthio group, halo $C_1$–$C_4$ alkylthio group, amino group and substituted amino group having 1 or 2 same or different substituents selected from the group consisting of $C_1$–$C_4$ alkyl and phenyl groups;

$Y^3$ represents
—O—,
—S— or
—N($R^8$)— in which $R^8$ is as defined above;

$X^3$ represents oxygen atom or sulfur atom;
m represents an integer of 0 to 5; and
p represents an integer of 0 or 1); and
letter a represents an integer of 1 to 30;
further, $R^3$ and $R^4$ may be taken conjointly to form a 3- to 8-membered ring including a $C_0$–$C_7$ alkylene group, and said 3- to 8-membered ring may be intercepted by
—O—,
—S(O)$_n$— in which n represents an integer of 0–2,
—N($R^8$)— in which $R^8$ is as defined above, or
—C($R^9$)($R^{10}$)— in which $R^9$ and $R^{10}$, same or different, represent halogen atom, $C_1$–$C_4$ alkyl group or a group of the following formula:

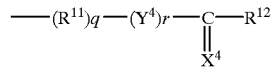

in which $R^{11}$, $R^{12}$, $X^4$, $Y^4$, q and r are as defined above; and $R^9$ and $R^{10}$ may be taken conjointly to form a 3- to 7-membered ring including a $C_2$–$C_6$ alkylene group; and R alternatively represents $C_0$–$C_{30}$ alkylene group which may be intercepted by one or more same or different group selected from the group consisting of
—O—,
—S(O)$_n$— in which n is as defined above,
—N($R^3$)— in which $R^3$ is as defined above,
—C($R^3$)=C($R^4$)— in which $R^3$ and $R^4$ are as defined above,

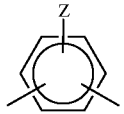

(Z represents hydrogen atom, dichloro group, dimethyl group, trimethyl group, tetramethyl group, halogen atom, nitro group, cyano group, hydroxyl group, mercapto group, $C_1$–$C_4$ alkyl group, halo $C_1$–$C_4$ alkyl group, $C_1$–$C_4$ alkoxy group, halo $C_1$–$C_4$ alkoxy group, $C_1$–$C_4$ alkylthio group, halo $C_1$–$C_4$ alkylthio group, amino group, substituted amino group having 1 or 2 same or different substituents selected from the group consisting of $C_1$–$C_4$ alkyl and phenyl groups, or a group of the following formula:

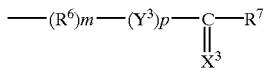

in which $R^6$, $R^7$, $Y^3$, $X^3$, m and p are as defined above) and

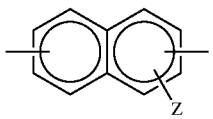

(Z is as defined above) provided that:

(1) when $R^1$ is defined as above, each of $X^1$ and $X^2$ is oxygen atom, $Y^1$ is oxygen atom or sulfur atom, $Y^2$ is $NR^3$ (wherein $R^3$ is defined as $R^3$ above), and R is $C_1$–$C_6$ alkylene group or

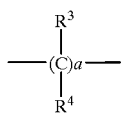

(wherein $R^3$ and $R^4$ represent hydrogen atom and letter a represents an integer of 1 to 6, or $R^3$ and $R^4$, same or different, represent $C_1$–$C_6$ alkyl group or phenyl group, and a is defined as above), then $R^2$ is not hydrogen atom, halogen atom or $C_1$–$C_6$ alkyl group;

(2) when $R^1$ is defined as above, each of $X^1$ and $X^2$ is oxygen atom, $Y^1$ is oxygen atom or sulfur atom, $Y^2$ is oxygen atom, and R is $C_1$–$C_{12}$ alkylene group or

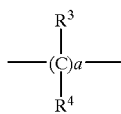

(wherein $R^3$ and $R^4$ represent hydrogen atom and letter a represents an integer of 1 to 12, or each of $R^3$ and $R^4$ is hydroxyl group, and a is defined as above), then $R^2$ is not hydrogen atom, halogen atom or $C_1$–$C_6$ alkyl group;

(3) when $R^1$ is defined as above, each of $X^1$ and $X^2$ is oxygen atom, $Y^1$ is $NR^3$ (wherein $R^3$ is defined as above), $Y^2$ is oxygen atom or —NH—, and R is

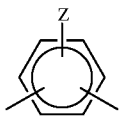

(wherein Z is hydrogen atom ), then $R^2$ is not hydrogen atom, halogen atom, or $C_1$–$C_6$ alkyl group; and (4) when $R^1$ is the same as defined above, each of $X^1$ and $X^2$ is oxygen atom, $Y^1$ is $NR^3$ (wherein $R^3$ is the same as defined above), $Y^2$ is —NH—, and R is $C_1$–$C_{12}$, alkylene group, or

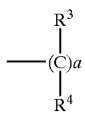

wherein $R^3$ and $R^4$ represent hydrogen atom and letter a represents an integer of 1 to 12,
then $R^2$ is not hydrogen atom, or halogen atom, $C_1$–$C_6$ alkyl group.

2. A bis-thiadiazole derivative or a salt thereof according to claim 1, wherein $R^1$ and $R^2$, same or different, represent hydrogen atom, $C_1$–$C_8$ alkyl group or halo $C_1$–$C_4$ alkyl group;

$X^1$ and $X^2$, same or different, represent oxygen atom or sulfur atom;

$Y^1$ and $Y^2$, same or different, represent oxygen atom, sulfur atom or

—$N(R^3)$— in which $R^3$ is as defined later; and

R represents $C_0$–$C_{30}$ alkylene group, an alkylene group represented by the following formula:

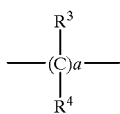

in which $R^3$ and $R^4$, same or different, represent hydrogen atom, halogen atom, nitro group, cyano group, $C_1$–$C_4$ alkyl group, $C_1$–$C_4$ alkoxy group, halo $C_1$–$C_4$ alkoxy group, $C_1$–$C_4$ alkylthio group, $C_1$–$C_4$ alkoxycarbonyl group, phenyl group, substituted phenyl group having 1 to 5 same or different substituents selected from the group consisting of halogen atom, nitro group, cyano group, hydroxyl group, mercapto group, $C_1$–$C_4$ alkyl group, halo $C_1$–$C_4$ alkyl group, $C_1$–$C_4$ alkoxy group, halo $C_1$–$C_4$ alkoxy group, $C_1$–$C_4$ alkylthio group, halo $C_1$–$C_4$ alkylthio group, amino group and substituted amino group having 1 or 2 same or different substituents selected from the group consisting of $C_1$–$C_4$ alkyl and phenyl groups, or a group of the following formula:

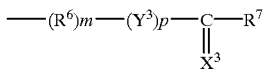

(wherein $R^6$ represents $C_1$–$C_6$ alkylene group, substituted $C_1$–$C_6$ alkylene group substituted by $C_1$–$C_4$ alkyl group, or $C_1$–$C_6$ alkylene group which may be intercepted by
—O— or
—S(O)$_n$— in which n is an integer of 0–2;

$R^7$ represents hydrogen atom, $C_1$–$C_8$ alkyl group, halo $C_1$–$C_8$ alkyl group, phenyl group, substituted phenyl group having 1 to 5 same or different substituents selected from the group consisting of halogen atom, nitro group, cyano group, hydroxyl group, mercapto group, $C_1$–$C_4$ alkyl group, halo $C_1$–$C_4$ alkyl group, $C_1$–$C_4$ alkoxy group, halo $C_1$–$C_4$ alkoxy group, $C_1$–$C_4$ alkylthio group, halo $C_1$–$C_4$ alkylthio group, amino group and substituted amino group having 1 or 2 same or different substituents selected from the group consisting of $C_1$–$C_4$ alkyl and phenyl groups, 5- or 6-membered heterocycle containing 1 to 3 hetero atoms selected from the group consisting of oxygen atom, sulfur atom and nitrogen atom, substituted 5- or 6-membered heterocycle containing 1 to 3 same or different hetero atoms selected from the group consisting of oxygen atom, sulfur atom and nitrogen atom and having, on the ring thereof, 1 to 5 same or different substituents selected from the group consisting of halogen atom, nitro group, cyano group, hydroxyl group, mercapto group, $C_1$–$C_4$ alkyl group, halo $C_1$–$C_4$ alkyl group, $C_1$–$C_4$ alkoxy group, halo $C_1$–$C_4$ alkoxy group, $C_1$–$C_4$ alkylthio group, halo $C_1$–$C_4$ alkylthio group, amino group and substituted amino group having 1 or 2 same or different substituents selected from the group consisting of $C_1$–$C_4$ alkyl and phenyl groups;

$Y^3$ represents
—O—,
—S— or
—N($R^8$)— in which $R^8$ represents hydrogen atom, halogen atom, $C_1$–$C_4$ alkyl group, halo $C_1$–$C_4$ alkyl group, $C_1$–$C_4$ alkoxycarbonyl group, phenyl group, substituted phenyl group having 1 to 5 same or different substituents selected from the group consisting of halogen atom, nitro group, cyano group, hydroxyl group, mercapto group, $C_1$–$C_4$ alkyl group, halo $C_1$–$C_4$ alkyl group, $C_1$–$C_4$ alkoxy group, halo $C_1$–$C_4$ alkoxy group, $C_1$–$C_4$ alkylthio group, halo $C_1$–$C_4$ alkylthio group, amino group and substituted amino group having 1 or 2 same or different substituents selected from the group consisting of $C_1$–$C_4$ alkyl and phenyl groups, phenyl $C_1$–$C_4$ alkyl group, substituted phenyl $C_1$–$C_4$ alkyl group having 1 to 5 same or different substituents selected from the group consisting of halogen atom, nitro group, cyano group, hydroxyl group, mercapto group, $C_1$–$C_4$ alkyl group, halo $C_1$–$C_4$ alkyl group, $C_1$–$C_4$ alkoxy group, halo $C_1$–$C_4$ alkoxy group, $C_1$–$C_4$ alkylthio group, halo $C_1$–$C_4$ alkylthio group, amino group and substituted amino group having 1 or 2 same or different substituents selected from the group consisting of $C_1$–$C_4$ alkyl and phenyl groups, or a group of the following formula:

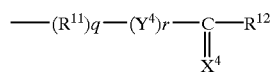

(wherein $R^{11}$ represents $C_1$–$C_6$ alkylene group or substituted $C_1$–$C_6$ alkylene group having one or more same or different substituents selected from the group consisting of halogen atom and $C_1$–$C_4$ alkyl group;

R represents hydrogen atom, $C_1$–$C_4$ alkyl group, halo $C_1$–$C_4$ alkyl group, phenyl group, substituted phenyl group having 1 to 5 same or different substituents selected from the group consisting of halogen atom, nitro group, cyano group, hydroxyl group, mercapto group, $C_1$–$C_4$ alkyl group, halo $C_1$–$C_4$ alkyl group, $C_1$–$C_4$ alkoxy group, halo $C_1$–$C_4$ alkoxy group, $C_1$–$C_4$ alkylthio group, halo $C_1$–$C_4$ alkylthio group, amino group and substituted amino group having 1 or 2 same or different substituents selected from the group consisting of $C_1$–$C_4$ alkyl and phenyl groups, 5- or 6-membered heterocycle containing 1 to 3 same or different hetero atoms selected from the group consisting of oxygen atom, sulfur atom and nitrogen atom, or substituted 5- or 6-membered heterocycle containing 1 to 3 same or different hetero atoms selected from the group consisting of oxygen atom, sulfur atom and nitrogen atom and having 1 to 4 same or different substituents selected from the group consisting of halogen atom, nitro group, cyano group, hydroxyl group, mercapto group, $C_1$–$C_4$ alkyl group, halo $C_1$–$C_4$ alkyl group, $C_1$–$C_4$ alkoxy group, halo $C_1$–$C_4$ alkoxy group, $C_1$–$C_4$ alkylthio group, halo $C_1$–$C_4$ alkylthio group, amino group and substituted amino group having 1 or 2 same or different substituents selected from the group consisting of $C_1$–$C_4$ alkyl and phenyl groups;

$Y^4$ represents —O—, —S— or —N($R^{13}$)— in which $R^{13}$ represents hydrogen atom or $C_1$–$C_4$ alkyl group;

$X^4$ represents oxygen atom or sulfur atom;

q represents an integer of 0 to 2; and r represents an integer of 0 to 1); and $X^3$ represents oxygen atom or sulfur atom;

m, same or different, represents an integer of 0 to 10; and p represents an integer of 0 or 1); and letter a represents an integer of 1 to 30; further $R^3$ and $R^4$ may be taken conjointly to form a 3- to 8-membered ring including a $C_0$–$C_7$ alkylene group, and said 3- to 8-membered ring may be intercepted by

—O—,

—S(O)$_n$— in which n is an integer of 0 to 2, or

—N($R^8$)— in which $R^8$ is as defined above, or a $C_0$–$C_{30}$ alkylene group which may be intercepted by one or more same or different groups selected from the group consisting of

—O—,

—S(O)$_n$— in which n is as defined above,

—N($R^3$)— in which $R^3$ is as defined above,

—($R^3$)═C($R^4$)— in which $R^3$ and $R^4$ are as defined above,

—C≡C—, and a group of the following formula:

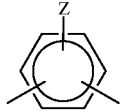

(Z represents halogen atom, nitro group, cyano group, hydroxyl group, mercapto group, $C_1$–$C_4$ alkyl group, halo $C_1$–$C_4$ alkyl group, $C_1$–$C_4$ alkoxy group, halo $C_1$–$C_4$ alkoxy group, $C_1$–$C_4$ alkylthio group, halo $C_1$–$C_4$ alkylthio group, amino group, substituted amino group having 1 or 2 same or different substituents selected from the group consisting of $C_1$–$C_4$ alkyl and phenyl groups, or a group of the following formula:

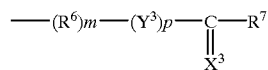

in which $R^6$, $R^7$, $Y^3$, $X^3$, m and p are as defined above).

3. A bis-thiazole derivative or a salt thereof according to claim 2, wherein $R^1$ and $R^2$, same or different, represent hydrogen atom, $C_1$–$C_8$ alkyl group or halo $C_1$–$C_4$ alkyl group;

$X^1$ and $X^2$, same or different, represent oxygen atom or sulfur atom;

$Y^1$ and $Y^2$, same or different, represent oxygen atom, sulfur atom or

—N($R^3$)— in which $R^3$ is as defined later; and

R represents $C_0$–$C_{30}$ alkylene group, an alkylene group represented by the following formula:

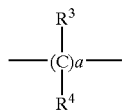

in which $R^3$ and $R^4$, same or different, represent hydrogen atom, halogen atom, nitro group, cyano group, $C_1$–$C_4$ alkyl group, $C_1$–$C_4$ alkoxy group, halo $C_1$–$C_4$ alkoxy group, $C_1$–$C_4$ alkylthio group, $C_1$–$C_4$ alkoxycarbonyl group, phenyl group or a group of the following formula:

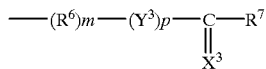

(wherein $R^6$ represents $C_1$–$C_6$ alkylene group, substituted $C_1$–$C_6$ alkylene group substituted by $C_1$–$C_4$ alkyl group, or $C_1$–$C_6$ alkylene group intercepted by
—O— or
—S(O)$_n$— in which n is an integer of 0–2;

$R^7$ represents hydrogen atom, $C_1$–$C_8$ alkyl group, halo $C_1$–$C_8$ alkyl group, phenyl group, substituted phenyl group having 1 to 5 same or different substituents selected from the group consisting of halogen atom, nitro group, cyano group, hydroxyl group, mercapto group, $C_1$–$C_4$ alkyl group, halo $C_1$–$C_4$ alkyl group, $C_1$–$C_4$ alkoxy group, halo $C_1$–$C_4$ alkoxy group, $C_1$–$C_4$ alkylthio group, halo $C_1$–$C_4$ alkylthio group, amino group and substituted amino group having 1 or 2 same or different substituents selected from the group consisting of $C_1$–$C_4$ alkyl and phenyl groups, 5- or 6-membered heterocycle containing 1 to 3 same or different hetero atoms selected from the group consisting of oxygen atom, sulfur atom and nitrogen atom, or substituted 5- or 6-membered heterocycle containing 1 to 3 same or different hetero atoms selected from the group consisting of oxygen atom, sulfur atom and nitrogen atom and having, on the ring thereof, 1 to 5 same or different substituents selected from the group consisting of halogen atom, nitro group, cyano group, hydroxyl group, mercapto group, $C_1$–$C_4$ alkyl group, halo $C_1$–$C_4$ alkyl group, $C_1$–$C_4$ alkoxy group, halo $C_1$–$C_4$ alkoxy group, $C_1$–$C_4$ alkylthio group, halo $C_1$–$C_4$ alkylthio group, amino group and substituted amino group having 1 or 2 same or different substituents selected from the group consisting of $C_1$–$C_4$ alkyl and phenyl groups;

$Y^3$ represents —O— or —S—;

$X^3$ represents oxygen atom or sulfur atom;

m, same or different, represents an integer of 0 to 10; and p represents an integer of 0 or 1); and letter a represents an integer of 1 to 30; and R alternatively represents a $C_0$–$C_{30}$ alkylene group which may be intercepted by one or more same or different groups selected from the group consisting of
—O—,
—S(O)$_n$— in which n is as defined above,
—N($R^3$)— in which $R^3$ is as defined above,
—C($R^3$)=C($R^4$)— in which $R^3$ and $R^4$ are as defined above,
—C≡C— or
a group of the following formula:

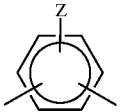

(Z is halogen atom, nitro group, cyano group, $C_1$–$C_4$ alkyl groups halo $C_1$–$C_4$ alkyl group, $C_1$–$C_4$ alkoxy group, halo $C_1$–$C_4$ alkoxy group, $C_1$–$C_4$ alkylthio group, halo $C_1$–$C_4$ alkylthio group or a group of the following formula:

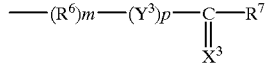

in which $R^6$, $R^7$, $Y^3$, $X^3$, m and p are as defined above).

4. An agrohorticultural disease controller which comprises the bis-thiadiazole derivative or a salt thereof according to any one of claims 1 to 3 as an active ingredient.

5. A method for controlling a plant disease which comprises treating a plant on which occurrence of plant disease is undesirable with an effective quantity of the agrohorticultural disease controller according to claim 4.

* * * * *